US012004935B2

(12) United States Patent
Kajanthan et al.

(10) Patent No.: US 12,004,935 B2
(45) Date of Patent: *Jun. 11, 2024

(54) ABSORBENT PAD FOR A GARMENT

(71) Applicant: MAS Innovation (Private) Limited, Battaramulla (LK)

(72) Inventors: Arulseelan Kajanthan, Dehiwala (LK); Lanka Buddhika Senanayake, Homagama (LK); Jalanthiran Selvarajah, Colombo (LK); Sumedha Kuruppu Arachchige, Homagama (LK); Mapitiyage Don Janith Dushyantha, Madapatha (LK); Kanishka Fernando, Katubadda (LK)

(73) Assignee: MAS Innovation (Private) Limited, Battaramulla (LK)

( * ) Notice: Subject to any disclaimer, the term of this patent is extended or adjusted under 35 U.S.C. 154(b) by 0 days.

This patent is subject to a terminal disclaimer.

(21) Appl. No.: 18/230,873

(22) Filed: Aug. 7, 2023

(65) Prior Publication Data

US 2023/0390127 A1  Dec. 7, 2023

Related U.S. Application Data

(63) Continuation of application No. 17/700,699, filed on Mar. 22, 2022, now Pat. No. 11,752,049, which is a
(Continued)

(30) Foreign Application Priority Data

Aug. 2, 2019  (GB) ...................................... 1911052

(51) Int. Cl.
*A61F 13/84* (2006.01)
*A41B 9/12* (2006.01)
(Continued)

(52) U.S. Cl.
CPC ............ *A61F 13/8405* (2013.01); *A41B 9/12* (2013.01); *A41D 31/10* (2019.02); *A41D 31/125* (2019.02);
(Continued)

(58) Field of Classification Search
CPC ........ A41B 9/12; A41D 31/10; A41D 31/125; A61F 13/4755; A61F 13/476;
(Continued)

(56) References Cited

U.S. PATENT DOCUMENTS 3,608,551 A   9/1971  Seijo
3,687,141 A   8/1972  Matsuda
(Continued)

FOREIGN PATENT DOCUMENTS

CA   2126280 A1   12/1994
CA   2126281 A1   12/1994
(Continued)

OTHER PUBLICATIONS

International Search Report in related application PCT/SG2020/050434 dated Oct. 15, 2020.
(Continued)

*Primary Examiner* — Michele Kidwell
(74) *Attorney, Agent, or Firm* — Patterson + Sheridan, LLP

(57) ABSTRACT

A garment having a fabric body and an absorbent pad attached to the fabric body is disclosed. The absorbent pad includes a liquid impermeable barrier layer and a functional layer attached to the barrier layer. The functional layer has a wicking component and a liquid absorbent component. The liquid absorbent component is disposed between the wicking component and the barrier layer. The absorbent pad is washable and reusable.

25 Claims, 13 Drawing Sheets

Related U.S. Application Data continuation of application No. 16/940,495, filed on Jul. 28, 2020.

(51) Int. Cl.
*A41D 31/10* (2019.01)
*A41D 31/12* (2019.01)
*A61F 13/49* (2006.01)
*A61F 13/494* (2006.01)
*A61F 13/515* (2006.01)
*A61F 13/537* (2006.01)
*A61F 13/56* (2006.01)
*A61F 13/66* (2006.01)

(52) U.S. Cl.
CPC ...... *A61F 13/49006* (2013.01); *A61F 13/494* (2013.01); *A61F 13/515* (2013.01); *A61F 13/537* (2013.01); *A61F 13/5616* (2013.01); *A61F 13/665* (2013.01); *A61F 2013/8408* (2013.01); *A61F 2013/8414* (2013.01)

(58) Field of Classification Search
CPC .............. A61F 13/49006; A61F 13/494; A61F 13/49446; A61F 13/49453; A61F 13/515; A61F 13/537; A61F 13/5616; A61F 13/665; A61F 13/8405; A61F 2013/8408; A61F 2013/8414
See application file for complete search history.

(56) References Cited

U.S. PATENT DOCUMENTS

| | | | |
|---|---|---|---|
| 3,838,693 A | 10/1974 | Sherman | |
| RE28,483 E | 7/1975 | Ralph | |
| 4,205,679 A | 6/1980 | Repke et al. | |
| 4,573,987 A | 3/1986 | Lamb, Jr. | |
| 4,641,381 A | 2/1987 | Heran et al. | |
| 4,664,663 A | 5/1987 | Brier | |
| 4,813,950 A | 3/1989 | Branch | |
| 4,898,594 A | 2/1990 | Cottenden | |
| 5,009,653 A | 4/1991 | Osborn, III | |
| 5,037,418 A | 8/1991 | Kons et al. | |
| 5,129,202 A | 7/1992 | Payne et al. | |
| 5,275,591 A | 1/1994 | Mavinkurve | |
| 5,291,617 A | 3/1994 | Moretz et al. | |
| 5,344,416 A | 9/1994 | Niihara et al. | |
| 5,546,607 A | 8/1996 | Roberts | |
| 5,562,648 A | 10/1996 | Peterson | |
| 5,591,147 A | 1/1997 | Couture-Dorschner | |
| 5,618,282 A | 4/1997 | Schlangen | |
| 5,651,779 A | 7/1997 | Burrell | |
| 5,669,902 A | 9/1997 | Sivilich | |
| 5,677,028 A | 10/1997 | Ravella | |
| 5,683,373 A | 11/1997 | Darby | |
| 5,879,487 A | 3/1999 | Ravella | |
| 6,013,062 A | 1/2000 | Dilnik | |
| 6,231,554 B1 | 5/2001 | Menard | |
| 6,381,994 B1 | 5/2002 | Lee | |
| 6,559,353 B1 | 5/2003 | Sheridan | |
| 6,602,236 B1 | 8/2003 | Mizutani | |
| 6,610,901 B2 | 8/2003 | Mcmahon-Ayerst et al. | |
| 6,848,121 B1 | 2/2005 | Halid | |
| 6,861,520 B1 | 3/2005 | Todd et al. | |
| 6,902,552 B2 | 6/2005 | VanGompel | |
| 7,008,887 B2 | 3/2006 | Rearick et al. | |
| 7,166,095 B1 | 1/2007 | Coates | |
| 7,337,914 B2 | 3/2008 | Spindel | |
| 7,842,625 B1 | 11/2010 | Stockton et al. | |
| 7,951,128 B1 | 5/2011 | Lewis | |
| 8,117,675 B2 | 2/2012 | Strange et al. | |
| D701,018 S | 3/2014 | Wexler | |
| 8,935,813 B2 | 1/2015 | O'Leary | |
| 8,968,266 B2 | 3/2015 | Kumar | |
| 9,011,403 B2 | 4/2015 | De Bruin et al. | |
| 10,342,266 B2 | 7/2019 | Oh | |
| 10,441,479 B2 | 10/2019 | Griffiths | |
| 10,441,480 B2 | 10/2019 | Griffiths | |
| 10,603,228 B2 | 3/2020 | Manabe | |
| 10,897,941 B1 | 1/2021 | Smoter | |
| 11,154,431 B1 | 10/2021 | Yip et al. | |
| 11,207,225 B2 | 12/2021 | Kajanthan et al. | |
| 11,752,049 B2* | 9/2023 | Kajanthan | A41D 31/10 604/359 |
| 2001/0016721 A1 | 8/2001 | Salerno et al. | |
| 2002/0035747 A1 | 3/2002 | Kusibojoska | |
| 2002/0053108 A1 | 5/2002 | Goyarts | |
| 2002/0068917 A1 | 6/2002 | VanGompel et al. | |
| 2002/0087139 A1 | 7/2002 | Popp | |
| 2004/0111074 A1* | 6/2004 | Eliasson | A61F 13/53743 604/367 |
| 2004/0230175 A1 | 11/2004 | Rainville-Lonn et al. | |
| 2005/0055002 A1 | 3/2005 | Whitelaw et al. | |
| 2005/0090795 A1 | 4/2005 | Coleman | |
| 2005/0273068 A1 | 12/2005 | Miskie | |
| 2006/0070163 A1 | 4/2006 | Beck | |
| 2006/0178652 A1 | 8/2006 | Miller, III | |
| 2008/0114327 A1 | 5/2008 | Barge | |
| 2008/0222781 A1 | 9/2008 | Rhew | |
| 2008/0275415 A1 | 11/2008 | Wheeler et al. | |
| 2008/0276352 A1 | 11/2008 | Strange et al. | |
| 2009/0082749 A1 | 3/2009 | Scott et al. | |
| 2010/0249736 A1 | 9/2010 | Png et al. | |
| 2011/0172621 A1 | 7/2011 | Lee et al. | |
| 2011/0268932 A1* | 11/2011 | Catalan | A61L 15/20 442/79 |
| 2012/0071849 A1 | 3/2012 | Kumar | |
| 2012/0180198 A1 | 7/2012 | Ruggieri | |
| 2013/0041339 A1 | 2/2013 | Taylor | |
| 2013/0046265 A1 | 2/2013 | Felix | |
| 2013/0053808 A1 | 2/2013 | Hill | |
| 2013/0072888 A1 | 3/2013 | Zorin | |
| 2014/0018756 A1 | 1/2014 | De Bruin | |
| 2014/0025027 A1 | 1/2014 | Png et al. | |
| 2014/0039432 A1 | 2/2014 | Dunbar et al. | |
| 2015/0290049 A1 | 10/2015 | Riha-Scott | |
| 2016/0089276 A1 | 3/2016 | Griffiths | |
| 2016/0184146 A1* | 6/2016 | Tulk | A01N 37/06 604/385.15 |
| 2018/0014983 A1 | 1/2018 | Jayasuriya et al. | |
| 2018/0092787 A1 | 4/2018 | Griffiths | |
| 2021/0030605 A1 | 2/2021 | Kajanthan | |
| 2021/0282469 A1 | 9/2021 | Siriwardena | |
| 2023/0082418 A1 | 3/2023 | Mellos | |

FOREIGN PATENT DOCUMENTS

| | | |
|---|---|---|
| CN | 100482119 C | 4/2009 |
| CN | 105748207 A | 7/2016 |
| CN | 107530208 A | 1/2018 |
| DE | 202004019377 U1 | 2/2005 |
| DE | 102008057840 A1 | 5/2010 |
| EP | 0490630 A1 | 6/1992 |
| EP | 0619953 A1 | 10/1994 |
| EP | 0689820 A1 | 1/1996 |
| EP | 1232735 A2 | 8/2002 |
| EP | 1351634 A1 | 10/2003 |
| EP | 2879534 A1 | 6/2015 |
| EP | 3437604 A1 | 2/2019 |
| EP | 3895675 A1 | 10/2021 |
| GB | 2130076 A | 5/1984 |
| JP | 2003227004 A | 8/2003 |
| JP | 2004105485 A | 4/2004 |
| JP | 2005111181 A | 4/2005 |
| JP | 2006002255 A | 1/2006 |
| JP | 2011144463 A | 7/2011 |
| JP | 2014201841 A | 10/2014 |
| JP | 2015029542 A | 2/2015 |
| JP | 2016005499 A | 1/2016 |
| KR | 100694187 B1 | 3/2007 |
| KR | 101875904 B1 | 7/2018 |
| KR | 101959502 B1 | 3/2019 |
| RU | 64902 U1 | 7/2007 |

(56) References Cited

FOREIGN PATENT DOCUMENTS

| | | |
|---|---|---|
| RU | 2400200 C1 | 9/2010 |
| WO | 86/05386 A1 | 9/1986 |
| WO | 98/43503 A1 | 10/1998 |
| WO | 2006073719 A2 | 7/2006 |
| WO | 2006/129550 A1 | 12/2006 |
| WO | 2010111717 A1 | 9/2010 |
| WO | 2014022832 A1 | 2/2014 |
| WO | 2014026236 A1 | 2/2014 |
| WO | 2015/039218 A1 | 3/2015 |
| WO | 2016133458 A1 | 8/2016 |
| WO | 2019/027318 A1 | 2/2019 |
| WO | 2019027318 A1 | 2/2019 |
| WO | 2021025615 A1 | 2/2021 |
| WO | 2021112695 A1 | 6/2021 |

OTHER PUBLICATIONS

European Search report in related application GB1911052.7 dated Jan. 9, 2020.
Nora Tagbinde Stay Dry Maxi; https://www.blumenkinder.eu/shop/Monatshygiene/Stoffbinden-Stoffslipeinlagen/nach-Art-und-Groesse/Fluegelbinden/Slipeinlagen/Tagbinden/Nora-Tagbinde-StayDry-maxi-4482.
Bloom and Nora Reusable Sanitary Pads for an Eco Friendly Period; www.totsbots.com/blog/blog-post/bloom-and-hora-reusable-sanitary-pads-for-an-eco-friendly-period.
Written Opinion in related application PCT/SG2020/050434 dated Feb. 11, 2021.
European Search in related application EP21176949.2 dated Sep. 17, 2021.
European Office Action in related application EP20754406.5 dated Oct. 22, 2021.
U.S. Office Action for related U.S. Appl. No. 17/190,245 dated May 24, 2021.
U.S. Office Action for related U.S. Appl. No. 17/190,245 dated Aug. 17, 2021.
Written Opinion of the ISA in related application PCT/SG2020/050434 dated Oct. 15, 2020.
European patent office Search Report in related application EP21176949.2 dated Sep. 17, 2021.
United Kingdom patent office search report in related application GB1911052.7 dated Jan. 9, 2020.
Boys Washable Absorbent Briefs https://bedwettingstore.com/products/boys-washable-absorbent-briefs-1.
Bruce Medical Supply, Hi-Cut Stay-Dry Briefs https://www.brucemedical.com/hicstaybrief.html.
Bryn, Finally, Some Oops-Free Underwear: Thank You OnGossamer Luxury Liner https://www.shefinds.com/finally_some_oops_free_underwear_thank_you_ongossamer_luxury_liner/.
Hinde, These Period Pants Stop Leaks So Women Can Get On With Their Lives Whether It's That Time Of The Month Or Not https://www.huffingtonpost.co.uk/2015/06/03/period-pants-thinx-invention_n_7499906.html.
Johnson, Can These Panties Disrupt The $15 Billion Feminine Hygiene Market https://www.forbes.com/sites/emmajohnson/2015/05/28/can-these-panties-disrupt-a-15-billion-feminine-hygiene-market/?sh=7426c0a53c5e.
Noman, Three Feminist Geniuses Just Invented a Pair of Panties That Could Change the World https://www.mic.com/articles/119796/this-new-magic-underwear-means-you-never-have-to-use-tampons-or-pads-again.
Kylie absorbent incontinence briefs https://www.kyliekanga.co.uk/washable-incontinence-underwear.
International Search Report dated Jul. 25, 2014 for PCT/CA/2014000389 filed on May 2, 2014.
Chinese Office Action for related application No. 202080053416.3 dated Jul. 13, 2022.
U.S. Office Action for related U.S. Appl. No. 17/700,699_dated Jun. 17, 2022.
Russian Office Action in related application RU20221021108 dated Jul. 12, 2022.
Further Examination Report for related GB application No. 2118915.4_dated Oct. 12, 2022.
Japanese Office Action for related JP application No. 2022-506616; dated Sep. 27, 2022.
U.S. Office Action for related U.S. Appl. No. 17/700,699; dated Oct. 20, 2022.

* cited by examiner

ABSORBENT PAD FOR A GARMENT

CROSS-REFERENCE TO RELATED APPLICATIONS

This application is a Continuation of U.S. patent application Ser. No. 17/700,699, filed on Mar. 22, 2022; application Ser. No. 17/700,699 is a Continuation of U.S. patent application Ser. No. 16/940,495, filed on Jul. 28, 2020; application Ser. No. 16/940,495 claims priority from U.K. Application No. 1911052.7, filed on Aug. 2, 2019 in the United Kingdom. Each of the above referenced patent applications is incorporated herein by reference its entirety.

BACKGROUND

Field

The present disclosure generally relates to an absorbent pad for a garment. More particularly, the present disclosure describes various embodiments of the absorbent pad for use in a garment as well as a garment comprising the absorbent pad.

Absorbent garments such as reusable and washable absorbent undergarments are worn with the purpose of absorbing bodily fluids. These bodily fluids include vaginal discharge, urine, menstrual fluid, sweat, and breast milk. Many people suffer from involuntary excretion of bodily fluids and there are few garments that have been designed to absorb such excretions that are functional and comfortable to the user wearing it.

For example, a woman who is menstruating will generally use a tampon or a sanitary pad, in addition to wearing an undergarment, to keep her outer garments from being soiled by menstrual fluid. While the tampon or pad often absorbs all the liquid flow, unexpected leaks can still occur. To avoid such leaks, she can instead choose to wear an adult brief, which offers a larger area of protection and may be particularly useful for women experiencing heavy menstrual flows. Adult briefs may also be useful for people who have urinary incontinence. However, adult briefs tend to be bulky and unattractive, making it difficult to conceal them under outer clothing, which may cause embarrassment to the user. Some disadvantages of wearing adult briefs and sanitary pads include prolonged exposure to wetness, which may result in discomfort, irritant dermatitis, and/or infections. Further, pads/tampons may be occasionally positioned incorrectly and adult briefs may be wrapped too loosely, both resulting in leakage. In addition, these conventional products are generally disposable, meaning that the environmental and economic costs can be significant.

The bulkiness of conventional products means that they do not allow the user to easily wear low-coverage undergarments. For example, absorbent pads must be placed into large, maximum-coverage undergarments that are capable of sufficiently containing them, while diapers and absorbent undergarments are generally large to adequately address the incontinence of the user. Therefore, someone who prefers thong-style or low-rise bikini underwear is often forced to choose between wearing preferred underwear, which risks leakage onto their outer clothing, or wearing a cumbersome and unattractive garment that would ensure that all leaks are prevented.

WO 2016/133458 describes an absorbent pad having a layered structure. However, this layered structure of the absorbent pad restricts how the absorbent pad can be fitted to a garment, namely by non-stitching means. DE 102008057840 describes an incontinence pad attached to a textile by sewing. However, sewing of the incontinence pad creates holes there though and these holes increase the risk of leakage.

Therefore, in order to address or alleviate at least one of the aforementioned problems and/or disadvantages, there is a need to provide an improved absorbent pad for use in a garment.

SUMMARY

According to a first aspect of the present disclosure, there is an absorbent pad for use in a garment. The absorbent pad comprises: a liquid impermeable barrier layer; a functional layer attached to the barrier layer, the functional layer comprising a liquid absorbent component; a liquid impermeable peripheral sealing element bonded to peripheries of the functional layer and barrier layer; and a peripheral attaching element having a first portion and a second portion, the first portion bonded to the peripheral sealing element, wherein the second portion of the peripheral attaching element is detached from the peripheral sealing element and is arranged to be attached to a fabric body of the garment, thereby attaching the absorbent pad to the garment.

According to a second aspect of the present disclosure, there is a method for forming an absorbent pad for use in a garment. The method comprises: attaching a functional layer to a liquid impermeable barrier layer, the functional layer comprising a liquid absorbent component; bonding a liquid impermeable peripheral sealing element to peripheries of the functional layer and barrier layer; and bonding a first portion of a peripheral attaching element to the peripheral sealing element, wherein a second portion of the peripheral attaching element is detached from the peripheral sealing element and is arranged to be attached to a fabric body of the garment, thereby attaching the absorbent pad to the garment.

According to a third aspect of the present disclosure, there is a garment comprising: a fabric body; and an absorbent pad attached to the fabric body. The absorbent pad comprises: a liquid impermeable barrier layer; a functional layer attached to the barrier layer, the functional layer comprising a liquid absorbent component; a liquid impermeable peripheral sealing element bonded to peripheries of the functional layer and barrier layer; and a peripheral attaching element having a first portion and a second portion, the first portion bonded to the peripheral sealing element, wherein the second portion of the peripheral attaching element is detached from the peripheral sealing element and is attached to the fabric body.

According to a fourth aspect of the present disclosure, there is a method for modifying a garment, the method comprising: providing a garment comprising a fabric body; and forming an absorbent pad for use in the garment. The absorbent pad comprises: a liquid impermeable barrier layer; a functional layer attached to the barrier layer, the functional layer comprising a liquid absorbent component; a liquid impermeable peripheral sealing element bonded to peripheries of the functional layer and barrier layer; and a peripheral attaching element having a first portion and a second portion, the first portion bonded to the peripheral sealing element, the second portion detached from the peripheral sealing element. The method further comprises attaching the second portion of the peripheral attaching element to the fabric body, thereby attaching the absorbent pad to the garment.

An absorbent pad for use in a garment according to the present disclosure is thus disclosed herein. Various features, aspects, and advantages of the present disclosure will become more apparent from the following detailed description of the embodiments of the present disclosure, by way of non-limiting examples only, along with the accompanying drawings.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

For purposes of brevity and clarity, descriptions of embodiments of the present disclosure are directed to an absorbent pad for use in a garment, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, known systems, methods, procedures, and components have not been described in detail so as to not unnecessarily obscure aspects of the embodiments of the present disclosure.

In embodiments of the present disclosure, depiction of a given element or consideration or use of a particular element number in a particular figure or a reference thereto in corresponding descriptive material can encompass the same, an equivalent, or an analogous element or element number identified in another figure or descriptive material associated therewith.

References to "an embodiment/example", "another embodiment/example", "some embodiments/examples", "some other embodiments/examples", and so on, indicate that the embodiment(s)/example(s) so described may include a particular feature, structure, characteristic, property, element, or limitation, but that not every embodiment/example necessarily includes that particular feature, structure, characteristic, property, element, or limitation. Furthermore, repeated use of the phrase "in an embodiment/example" or "in another embodiment/example" does not necessarily refer to the same embodiment/example.

The terms "comprising", "including", "having", and the like do not exclude the presence of other features/elements/steps than those listed in an embodiment. Recitation of certain features/elements/steps in mutually different embodiments does not indicate that a combination of these features/elements/steps cannot be used in an embodiment. The terms "a" and "an" are defined as one or more than one. The use of "/" in a figure or associated text is understood to mean "and/or" unless otherwise indicated. The recitation of a particular numerical value or value range herein is understood to include or be a recitation of an approximate numerical value or value range.

Figure 1:
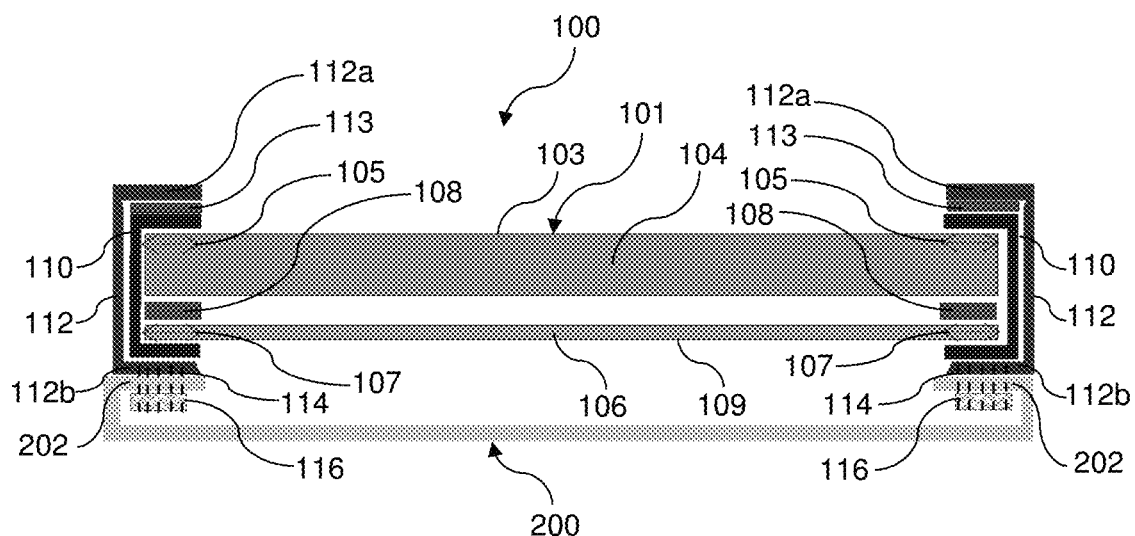
FIG. 1 is a cross-sectional illustration of an absorbent pad attached to a fabric body of a garment, in accordance with some embodiments of the present disclosure.

In representative or exemplary embodiments of the present disclosure, there is an absorbent pad or pad 100, such as in but not limited to the form of a gusset, for use in a garment as illustrated in FIG. 1. Specifically, the absorbent pad 100 is attachable to a fabric body 200 of the garment. The garment may be an intimate garment or undergarment worn by a user particularly at parts of the body where there may be excretions of bodily fluids. For example, the garment may be, but is not limited to brassieres, lingerie, sportswear, and similar close-fitting or form-fitting garments. The absorbent pad 100 includes a functional layer 101 and a liquid impermeable barrier layer 106, wherein the functional layer 101 is attached, such as by bonding and/or stitching, to the barrier layer 106. The functional layer 101 includes a liquid absorbent component 104 capable of absorbing liquid.

Figure 2:
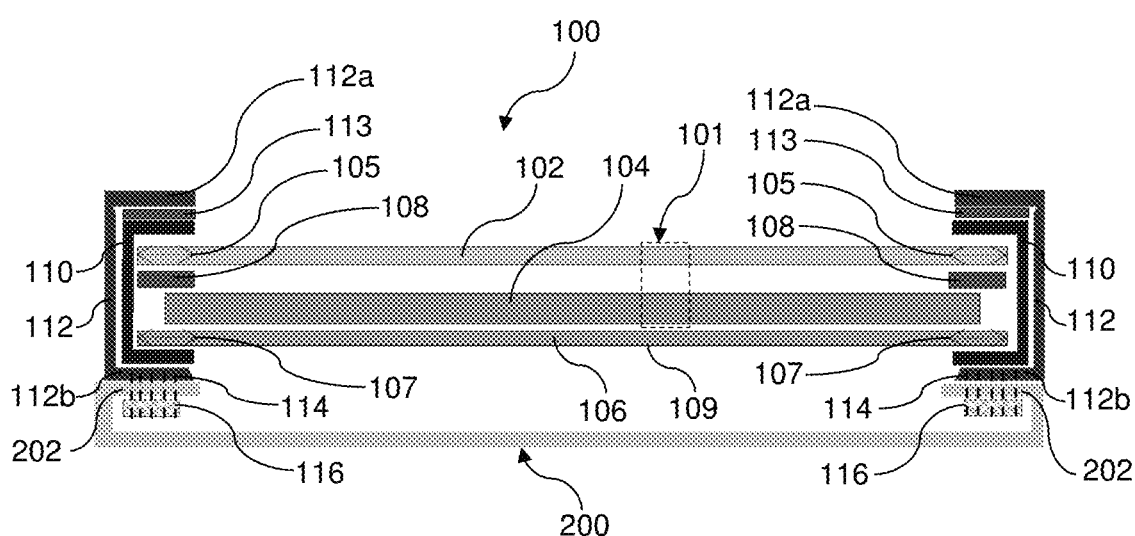
FIG. 2 is another cross-sectional illustration of an absorbent pad attached to a fabric body of a garment, in accordance with some embodiments of the present disclosure.

In some embodiments as shown in FIG. 2, the functional layer 101 further includes a liquid permeable wicking component 102, wherein the absorbent component 104 is attached, such as by bonding and/or stitching, to the wicking component 102 and disposed between the wicking component 102 and the barrier layer 106. Additionally, the functional layer 101 is attached, such as by bonding and/or stitching, to the barrier layer 106 at the wicking component 102.

The wicking component 102 is capable of acquiring and distributing liquid or moisture to the underlying absorbent component 104. Specifically, when the garment comprising the absorbent pad 100 is worn by the user, the wicking component 102 faces the user's body and serves to transport bodily fluids produced by the user's body to the absorbent component 104. In other words, the wicking component 102 transport liquid from its surface that is in direct contact with the user to its internal surface that is in contact with the absorbent component 104. The wicking component 102 may be made from fibres or yarns made with fibres, where said fibres and yarns are selected from one or more of the group consisting of polyamide, polyester, polyolefin, polyurethane, polyacrylonitrile, natural cellulose, regenerated cellulose, regenerated cellulose derivatives (i.e. cellulose acetate and cellulose triacetates), natural protein and regenerated protein. The wicking component 102 may be produced using technologies such as knitting (warp knitting such as raschel Tricot, weft knitting such as circular or flat), weaving, non-woven methods (blow spinning, staple nonwoven, spun laid, air-laid, needle punched, thermal bonded, hydro-entangled, chemical bonded and so forth), electrospinning, force-spinning etc. Additionally, the wicking component 102 may also include one or more of the coatings, treatments encapsulation or entrapments, which would enhance its liquid and moisture management functionality, such as rate of wicking, wicking capacity, rate of spreading and distribution, one-way liquid transport etc.

The material of the wicking component 102 may be naturally moisture-wicking and/or be treated to become moisture-wicking. For example, the wicking material may be 100% polyester fabric with French Terry knit and a denier differential across the two faces of the wicking component 102 that assists in moving the liquid from the skin-facing side of the wicking component 102 to the internal surface that is in contact with the absorbent component 104. Other suitable wicking materials include blends of polyester, polypropylene, and cotton. An advantage associated with the use of a wicking component 102 having the triangular ridge structures of French Terry knitting facing the user's skin is that less surface area of the surface of the wicking component 102 comes into contact with the skin and therefore reduces any sensation of feeling wetness against the skin.

As an example, the wicking component 102 may comprise a material that is 51% cotton and one or both of the inner and outer surfaces of the wicking component 102 may be treated with a hydrophilic composition or material (e.g. polyethylene oxide, polyvinyl alcohol, polyacrylamide, poly acrylic acid, polyvinyl pyrrolidone, hydrophilic silicones, or hydrophilic polyurethanes) and/or a hydrophobic composition or material (e.g. silicones, polyfluoroalkylacrylates, polyacrylates, polyurethanes, or waxes) to create a net hydrophilic gradient across the wicking component 102. In other words, the surface in direct contact with the user's skin may be less hydrophilic (i.e. more hydrophobic) whereas the outer surface may be more hydrophilic. For example, the surface of the wicking component 102 in direct contact with the user's skin may be treated with a hydrophobic material and/or the opposing surface may be treated with a hydrophilic material. This results in a combination of a "pushing" force generated by the hydrophobic properties of the surface in direct contact with the user's skin and a "pulling" force generated by the hydrophilic properties of the outer surface that may wick any moisture or liquid through the wicking component 102 and away from the user. The hydrophilic and hydrophobic compositions may be applied to the wicking component 102 using any conventional method known to the skilled person.

Additionally, the differential capillary forces on either side can be created by the fabric structure of the wicking component 102 where one side of the wicking component 102 has a smaller pore size in comparison to the opposite side of the wicking component 102. Ideally, this pore combination creates funnel-like structures through the wicking component 102 in cross-section, where the liquid is pulled from the side with the larger pore size to the side with the smaller pore size, due to the differential capillary pressure.

The rate of wicking through the wicking component 102 may be controlled to be faster or slower. The rate may be set at a maximum rate of absorption of the wicking component 102 to ensure that all, or a significant percentage of, the liquid is absorbed by the absorbent component 104 and does not leak beyond the confines of the garment. The rate of wicking may be controlled by the density, thickness, or composition of the wicking component 102 and/or by the amount and type of hydrophobic and/or hydrophilic material applied to the wicking component 102. In another embodiment, the rate of wicking may be set such that the surface of the wicking component 102 in direct contact with the user feels "dry" or mostly dry to the user while the other surface may feel wet.

In some embodiments, the wicking component 102 may include an antimicrobial agent or substance. For example, the antimicrobial substance may be one or more substances selected from the group consisting of a silver-containing substance, titanium dioxide, a quaternary silane, hydrogen peroxide, triclosan, and zinc pyrithione. Additionally or alternatively, the wicking component 102 may include an agent or substance that combats odour. For example, the substance that combats odour may be one or more substances selected from the group consisting of nanoparticles with acid-neutralising pockets, high surface area mineral compositions, high surface area ceramic compositions and high surface area clay compositions. Further additionally or alternatively, the wicking component 102 may include a stain-resistant or stain-proof agent or substance.

The absorbent component 104 may include any liquid absorbent/absorbing material known in the art (e.g. cotton, a cotton blend, foam, a synthetic material, absorbent polymeric foam, a nanotechnology-based or -produced material, or any other moisture-absorbent material). The material may have a weight of 50 to 500 $g/m^2$, such as 180 to 300 $g/m^2$. For example, the absorbent component 104 may be made from an 80:20 blend of polyester:nylon fabric with a microfiber double terry knit. Other suitable materials include polypropylene or any cellulose-based fabric and their blends including cotton, bamboo etc.

In some embodiments, the absorbent component 104 may be a 100% polyester double terry fabric. This material is approximately 90% air and so allows for a higher absorbent capacity, as moisture fills up the air gaps of the polyester terry fabric without significant expansion of the polyester fibres. This does not translate into significantly thicker absorbent pad 100.

In some embodiments, the absorbent component 104 may be made from a blended fibre comprising two or more of superabsorbent polymer (SAP), hydrogel and polyester, or at least part (e.g. the surface facing towards the fabric body 200 of the garment) of the absorbent component 104 may have been treated with SAP and/or hydrogel. In these embodiments, the use of these materials may result in increased liquid absorbent capacity, with a reduced thickness and weight for the absorbent pad 100, and in an improved dry feel on the surface of the wicking component 102 in contact with the user's skin, due to an increased affinity in the absorbent component 104.

In some embodiments as shown in FIG. 1, the functional layer 101 includes the absorbent component 104 but excludes the wicking component 102. In some embodiments, the functional layer 101 is treated such that it also achieves at least some properties of the wicking component 102 as described above. Specifically, the outer surface 103 of the functional layer 101 may be chemically treated such that the outer surface 103 enables liquid to be transported efficiently to the underlying absorbent component 104. Such chemical treatments will be readily known to the skilled person. The treated outer surface 103 thus achieves the properties of the wicking component 102 as described above for acquiring and distributing liquid to the absorbent component 104. The functional layer 101 may additionally be treated or added with agents/substances such that it contains one or more of an antimicrobial agent, an odour-combatting agent, and a stain-resistant agent, such as those described above for the wicking component 102 to achieve the associated properties.

The barrier layer 106 is leak-proof and may include any known wholly or partially liquid-blocking material. Preferably, the barrier layer 106 is breathable, so that liquid may not pass through it, but gases (including water vapour) can do so. For example, the barrier layer 106 may include one or more layers of a thermoplastic or thermoset film, where the thermoplastic or thermoset film is selected from one or more of the group consisting of polyurethane, polyester, polyolefin, and silicone. Particular examples of liquid impermeable materials include layers made from a liquid impermeable polymer or a thermoplastic polyurethane film.

In some embodiments, the barrier layer 106 may be a lightweight tightly knitted/woven fabric coated with SAP/hydrogel, or the barrier layer 106 may be a lightweight tightly knitted/woven fabric made using textile/SAP hybrid fibres. Alternatively, the barrier layer 106 may be a liquid-proof membrane (such as a liquid-proof membrane material supplied by Dingzing Advanced Materials Inc, Taiwan). When used in a garment comprising the absorbent pad 100, the barrier layer 106 may provide the advantage of being fully breathable in dry form, while providing an effective barrier material upon exposure to liquid. Furthermore, these materials may also enable the absorbent pad 100 to dry more quickly than the use of a liquid impermeable polymer such as a thermoplastic polyurethane film.

In some embodiments as shown in FIG. 1, the functional layer 101 is bonded to the barrier layer 106 at their respective peripheries or side edges by a bonding means 108. Alternatively, the bonding means 108 may be applied across the entire surfaces between the functional layer 101 and barrier layer 106. The bonding means 108 may be an adhesive or ultrasonic bonding. For example, the adhesive may be an adhesive tape, liquid glue, or hotmelt powder glue). When the adhesive is an adhesive tape, the tape is a double-sided adhesive tape (such as of the type produced by Bemis Associates Inc.) and said tape may have a single layer or multiple layers where said multiple layers may have one or more functions, such as barrier layers, elastic layers etc. When the adhesive is a liquid glue, the glue may be a hot melt glue, a liquid resin or combinations thereof (e.g. the adhesive may be a hot melt glue/liquid resin bonding by nozzle extrusion or liquid resin bonding by screen printing/template printing).

In some embodiments as shown in FIG. 2, the functional layer 101 includes the wicking component 102 attached, such as by bonding and/or stitching, to the absorbent component 104. The absorbent component 104 and barrier layer 106 may be bonded to the wicking component 102 at their respective peripheries or side edges by the bonding means 108. Optionally, the absorbent component 104 may be bonded to the barrier layer 106 with the bonding means 108 applied across the entire surfaces between them.

The functional layer 101 and barrier layer 106 may have the same 2D footprint, meaning that the shape or area of each layer 101 and 106 is substantially identical when viewed from above/below the plane on which the layers 101 and 106 lie. In embodiments where the functional layer 101 includes the wicking component 102 and absorbent component 104, while the 2D footprints of the functional layer 101 and barrier layer 106 are essentially the same size, the absorbent component 104 has a 2D footprint that is smaller than the 2D footprints of the wicking component 102 and barrier layer 106. For example, the 2D footprint of the absorbent component 104 is approximately 2 to 20 mm, such as 10 to 15 mm, smaller around its periphery than the 2D footprints of the wicking component 102 and barrier layer 106. This difference in size may allow the functional layer 101 (including the differentially sized wicking component 102 and absorbent component 104) and barrier layer 106 to be unified into a single pad by a single bonding means 108. Using a single bonding means 108 for unifying the various layers/components may advantageously mitigate the risk of leakage.

It will be appreciated that there could be other possible arrangements of the layers/components, with the bonding means 108 being applied as appropriate. For example, the wicking component 102, absorbent component 104, and barrier layer 106 are bonded together by a single adhesive tape. Alternatively, the wicking component 102 is bonded to the absorbent component 104 by a first adhesive tape and the wicking component 102 is bonded to the barrier layer 106 by a second adhesive tape. A third adhesive tape may also be used to bond the absorbent component 104 to the barrier layer 106.

In another exemplary arrangement of the layers/components, the respective 2D footprints may increase from the wicking component 102 (smallest area) to the absorbent component 104 and then to the barrier layer 106 (largest area). It will be appreciated that the bonding means 108 may be applied as appropriate to bond the various layers/components together.

The absorbent pad 100 further includes a liquid impermeable peripheral sealing element 110 surrounding the peripheries of the functional layer 101 and barrier layer 106. Specifically, the peripheral sealing element 110 is bonded to a periphery 105 of the functional layer 101 and a periphery 107 of the barrier layer 106. Notably, the periphery 105 of the functional layer 101 may be at the side edge of the exposed wicking component 102 or outer surface 103, and the periphery 107 of the barrier layer 106 may be likewise at the side edge of the exposed surface 109 of the barrier layer 106.

The peripheral sealing element 110 may include a single-sided adhesive tape such as of the type produced by Bemis Associates Inc. and said tape may have a single layer or multiple layers where said multiple layers may have one or more functions, such as barrier layers, elastic layers etc. The adhesive side of the single-sided adhesive tape faces the functional layer 101 and barrier layer 106. As shown in FIG. 1 and FIG. 2, the peripheral sealing element 110 has a C-fold or C-shaped arrangement that entirely encloses the peripheries 105 and 107 of the functional layer 101 and barrier layer 106, respectively. This arrangement forms a liquid impenetrable barrier seal or cuff around the periphery of the absorbent component 104, advantageously reducing the leakage from the resulting absorbent pad 100 onto the garment. This arrangement also results in a durable garment that may be washed and reused.

In some embodiments, the peripheral sealing element 110 is a liquid impermeable element without adhesive properties. The peripheral sealing element 110 may be bonded to the periphery 105 of the functional layer 101 and the periphery 107 of the barrier layer 106 by suitable bonding means, such as adhesive or ultrasonic bonding. It will be appreciated that in various embodiments, the peripheral sealing element 110 may be bonded to all layers/components of the absorbent pad 100.

In some embodiments, the functional layer 101 is attached to the barrier layer 106 by stitching at their respective peripheries 105,107, instead of bonding using the bonding means 108. Similarly, the wicking component 102, absorbent component 104, and barrier layer 106 can be stitched together at the peripheries 105,107. However, these stitches could potentially form conduits for liquid to pass through the barrier 106. The peripheral sealing element 110 is thus arranged such that it overlaps the stitches at the peripheries 105,107 in order to maintain the liquid impermeability of the absorbent pad 100.

In some embodiments, the barrier layer 106 and peripheral sealing element 110 may be a continuous piece of liquid impermeable material, i.e. there is no bonding at the periphery 107. This continuous material would be bonded to the periphery 105 of the functional layer 101 in a similar manner to the embodiments where the barrier layer 106 and peripheral sealing element 110 are separate pieces of material bonded together.

The absorbent pad 100 further includes a peripheral attaching element 112 having a first portion 112a and a second portion 112b. The peripheral attaching element 112 may be formed of a suitable material that may optionally be elastic to facilitating attaching to the fabric body 200. The peripheral attaching element 112 may be formed of the same, similar, or different fabric or textile material as that of the fabric body 200. The first portion 112a of the peripheral attaching element 112 is arranged adjacently to the functional layer 101 and bonded to the peripheral sealing element 110. In some embodiments, said bonding of the first portion 112a is achieved by use of a bonding means 113 that is similar to the bonding means 108 described above. For example, the bonding means 113 is a double-sided adhesive tape such as of the type produced by Bemis Associates Inc. and said tape may have a single layer or multiple layers where said multiple layers may have one or more functions, such as barrier layers, elastic layers etc. In some embodiments, said bonding is achieved by ultrasonic bonding or an adhesive such as liquid glue or hotmelt powder glue. When the adhesive is a liquid glue, the glue may be a hot melt glue, a liquid resin or combinations thereof (e.g. the adhesive may be a hot melt glue/liquid resin bonding by nozzle extrusion or liquid resin bonding by screen printing/template printing).

The second portion 112b of the peripheral attaching element 112 is arranged adjacently to the barrier layer 106 and detached from the peripheral sealing element 110. As mentioned above, the peripheral sealing element 110 can be a single-sided adhesive tape and the adhesive side faces the barrier layer 106 while the non-adhesive side faces the second portion 112b. Moreover, as the bonding means 113 is applied between the first portion 112a and functional layer 101 and not to the second portion 112b, there are no adhesive or bonding properties on the second portion 112b. Thus, the second portion 112b is detached from and not bonded to the peripheral sealing element 110.

The second portion 112b is arranged to be attached to the fabric body 200 of the garment, such as by stitching, sewing, and/or bonding means (or any combination thereof), thereby attaching the absorbent pad 100 to the garment. As the second portion 112b is detached from the peripheral sealing element 110, it is positioned freely to be attached to the fabric body 200 with minimal constraints. For example, the second portion 112b may be stitched or sewed to the fabric body 200 and the detached second portion 112b allows for easier stitching, sewing, and/or bonding to the fabric body 200. This arrangement thus allows the second portion 112b to function as a fabric strip or flap for attaching the absorbent pad 100 to a garment. Moreover, by using a freely mobile fabric strip or flab to attach to the fabric body 200, no stitching or sewing is required at other layers/components of the absorbent pad 100, such as stitches through the functional layer 101 or peripheral sealing element 110, thus minimizing risk of leakage through the absorbent pad 100.

As shown in FIG. 1 and FIG. 2, the peripheral attaching element 112 may have a C-fold or C-shaped arrangement, like that of the peripheral sealing element 110, that entirely encloses the peripheral sealing element 110. This arrangement forms a fabric cover over the peripheral sealing element 110, thereby protecting it and improving the texture and feel of the absorbent pad 100. It will be appreciated that the peripheral attaching element 112 may be arranged differently while keeping the first portion 112a and second portion 112b bonded to and detached from, respectively, the peripheral sealing element 110.

Figure 3:
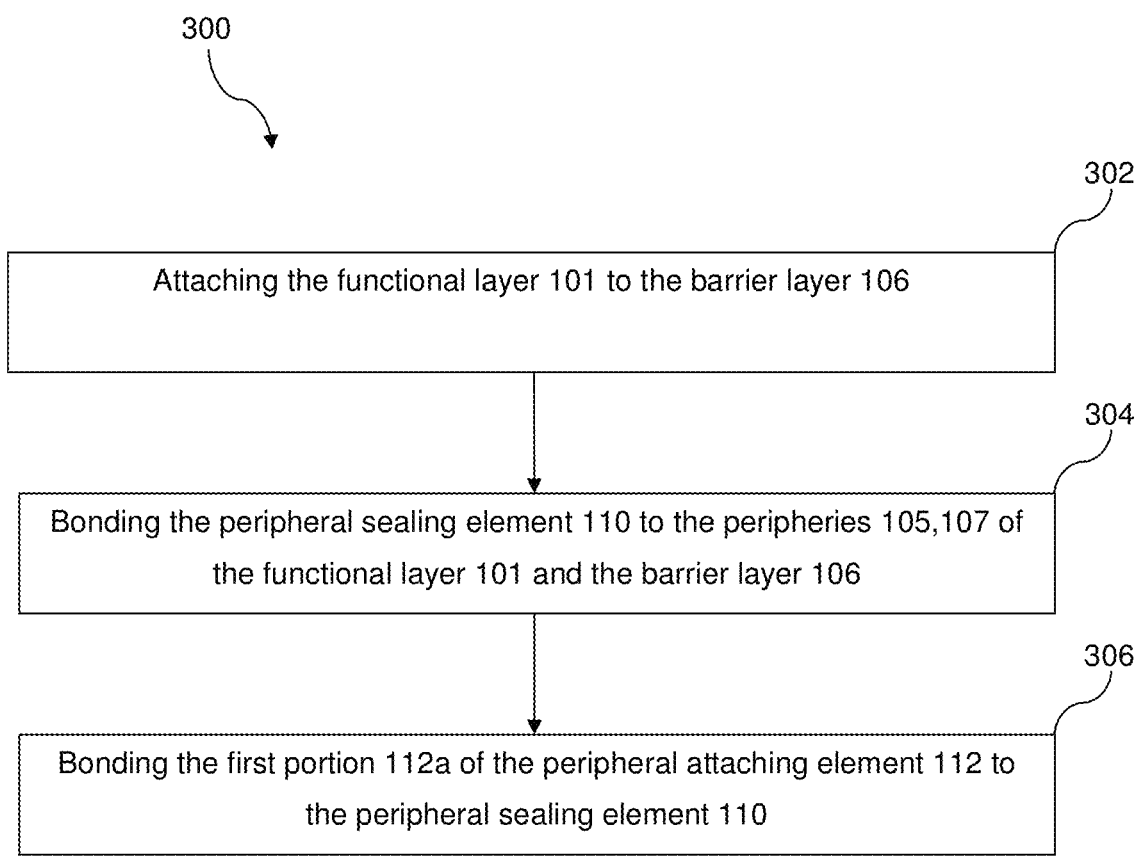
FIG. 3 is a flowchart illustration of a method for forming the absorbent pad, in accordance with some embodiments of the present disclosure.

In various embodiments of the present disclosure, there is a method 300 for forming the absorbent pad 100. With reference to FIG. 3, the method 300 includes a step 302 of bonding the functional layer 101 to the barrier layer 106. The method 300 further includes a step 304 of bonding the peripheral sealing element 110 to the periphery 105 of the functional layer 101 and the periphery 107 of the barrier layer 106. The method 300 further includes a step 306 of bonding the first portion 112a of the peripheral attaching element 112 to the peripheral sealing element 110. The second portion 112b of the peripheral attaching element 112 is detached from the peripheral sealing element 110 and is arranged to be attached to the fabric body 200 to thereby attach the absorbent pad 100 to the garment.

It will be appreciated that various aspects of the absorbent pad 100 described above apply similarly or analogously to the method 300 for forming the absorbent pad 100 and will not be further described for purpose of brevity.

Figure 4A:
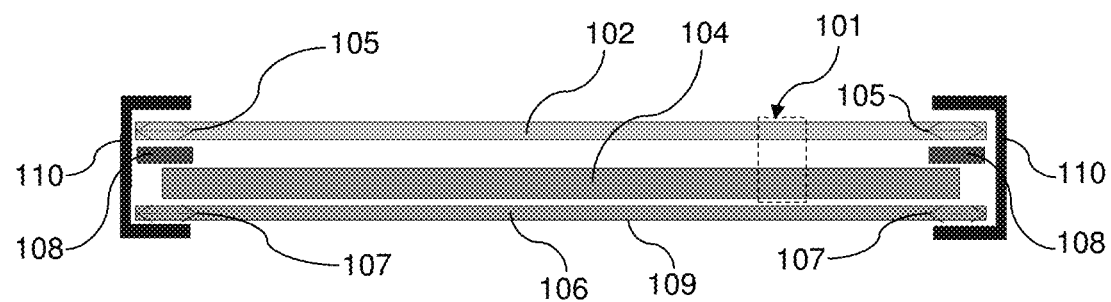
FIG. 4A to FIG. 4D are various cross-sectional and plan view illustrations of the absorbent pad being formed, in accordance with some embodiments of the present disclosure.
Figure 4B:
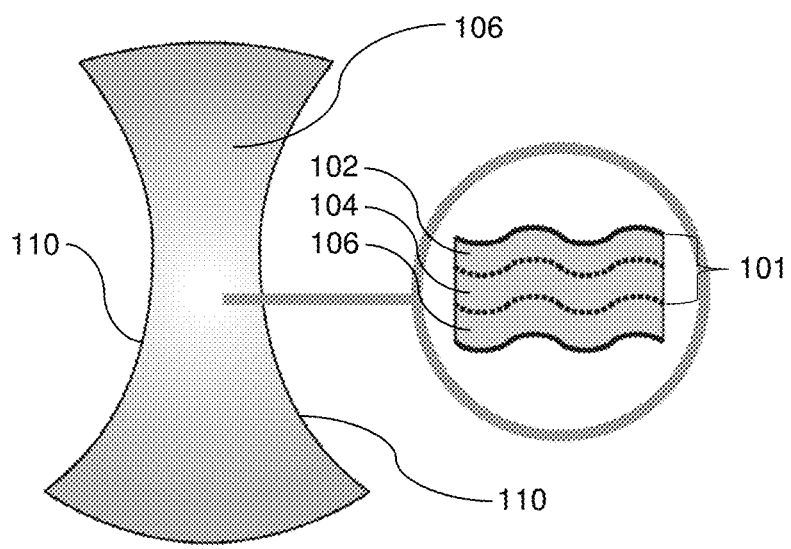

In some embodiments, the functional layer 101 includes the wicking component 102 and absorbent component 104. The step 302 may include attaching, such as by bonding and/or stitching, the wicking component 102 to the absorbent component 104 and the barrier layer 106, such that the absorbent component 104 is disposed between the wicking component 102 and the barrier layer 106. For example, the wicking component 102, absorbent component 104, and barrier layer 106 are bonded together by the bonding means 108. The step 304 may include bonding the peripheral sealing element 110 to the respective peripheries of the wicking component 102 and the barrier layer 106. The steps 302 and 304 thus combine the various layers/components into a layer composite as shown in FIG. 4A and FIG. 4B.

Figure 4C:
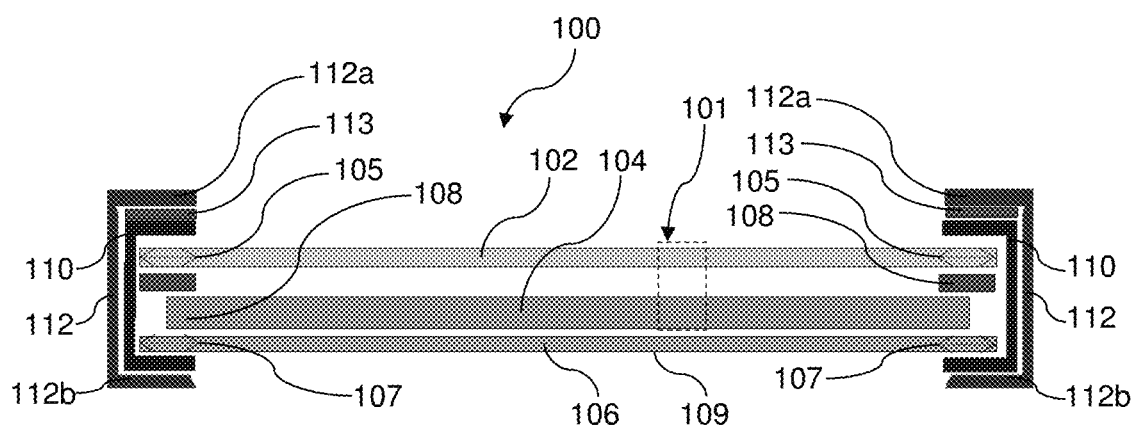
Figure 4D:
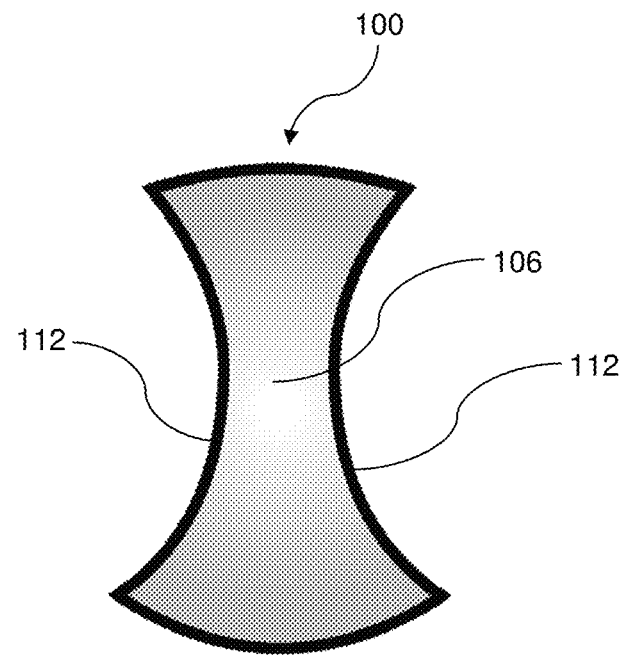

In the step 306, the first portion 112a of the peripheral attaching element 112 is bonded to a portion of the peripheral sealing element 110. The peripheral attaching element 112 may be in the form of a fabric strip cut covering the outer edges of the functional layer 101/wicking component 102 and the barrier layer 106. The steps 302 to 306 thus result in the forming of the absorbent pad 100 as shown in FIG. 4C and FIG. 4D. The absorbent pad 100 is structured such that the liquid impermeable layers/components thereof are joined by suitable bonding means, such as adhesive or ultrasonic bonding and without stitching or sewing. The absence of stitches thus minimizes the risk of leakage through the absorbent pad 100.

In various embodiments of the present disclosure as shown in FIG. 5 and FIG. 6A to FIG. 6F, there is a garment 400 and a method 500 for modifying the garment 400. The garment 400 includes the fabric body 200 and the absorbent pad 100 attached to the fabric body 200.

Specifically, the absorbent pad 100 is attached to an interior surface of the fabric body 200 and extends over at least an area of the user that is subject to bodily excretions. One or more absorbent pads 100 may form part of a garment, whether integral or removable. Any garment that is intended to be in contact with a user's skin may be fitted with one or more absorbent pads 100. For example, the garment may be outerwear, such as a shirt, a T-shirt, shorts, trousers/pants, leggings, running shorts, bicycle shorts, swimwear, yoga pants, body-shape-altering "stretch" pants, shorts etc. In particular, the garment may be sportswear or an undergarment (e.g. bra or underpants, sport or "performance" underwear). One or more absorbent pads 100 may be fitted to cover a small area of the garment, which will generally be an area subject to the production of bodily excretions, such as the crotch area, the underarm area and the nipples of a pre- or post-partum female. Alternatively, the absorbent pads 100 may cover a major portion of the internal surface area of the garment, for example, the absorbent pads 100 in a pair of underpants may cover from 30-100% of the internal surface area of the garment. The level of internal surface area coverage of the absorbent pads 100 can be readily determined by the skilled practitioner based upon the intended use and the desired level of comfort of the user.

In some embodiments, the garment may be a pair of underpants. The underpants include a fabric body 200 having a waist opening and a pair of leg openings defining a crotch area there between that covers some or all of the genital area of a user. The underpants contain an internal surface that is in contact with the user's skin (in this case the genital area of the wearer) and an external surface, where some or all of said external surface is not in direct contact with the user's skin. The underpants also include an absorbent pad 100 that is attached to the interior surface of the fabric body 200, specifically by stitching. The absorbent pad 100 may be disposed to cover the crotch area and may extend over some or all of the crotch area and/or extend beyond the crotch area. It will be appreciated that the underpants may be of any cut, size, style, colour, and type.

The fabric body 200 may contain one or more layers. For example, when the fabric body 200 contains one layer, the absorbent pad 100 can be attached to the crotch area of the fabric body 200. When the fabric body 200 contains two layers, there is an inner fabric-body layer that wholly or partially contacts the body of the user and an outer fabric-body layer that is not in contact with the body of the user. The outermost fabric-body layer may be one or more of various colours, patterns, or designs (e.g., black, white, pink, etc.) to provide choices to the user, though for a fabric body 200 containing a single layer a dark colour may be preferred. When the fabric body 200 comprises more than one layer, the innermost fabric-body layer may be a dark colour (e.g., black or dark grey) to help provide stain-resistance, so that any stain thereon is invisible or reduced in visibility or noticeability to the user. If the fabric body 200 contains two or more layers, all, some, or none of the inner layer or layers may be visible to the user or other observer when the garment worn. Any of the layers may be cut to the same size of the outer fabric-body layer or can be cut to less than the full size of said layer.

When the fabric body 200 has a single fabric-body layer, the material may be made of cotton, a cotton blend, a synthetic material, an elasticized blend (e.g. SPANDEX) or any other material (e.g. natural or man-made textile). When the fabric body 200 has two or more layers, the inner layers may be made of a thin fabric, while the outermost layer may be made of a thicker fabric, such as those described above. The inner fabric-body layer(s) may be cut to the full shape of the fabric body 200 or be cut to less than the full shape of the fabric body 200. For example, if the garment is a pair of underpants, an inner fabric-body layer may be cut to extend to cover only the crotch region. The inner fabric-body layer may also be densely stitched to the inner surface of the outer fabric-body layer to prevent leakage of fluids from the body of the user onto the outer surface of the underpants (or onto the wearer's outer clothes) and/or to any point on the inner surface of the underpants outside of the crotch area that may be felt or by the user. The underpants can be in any style. For example, the underpants may have a low-cut style where the waistband is lower than the user's waist (typically, at a location at or near the hips of the user) or the underpants can have a high cut, such that they include a section of fabric that extends above the waistband. It will be appreciated that any suitable height of waistband may be used.

Figure 5:
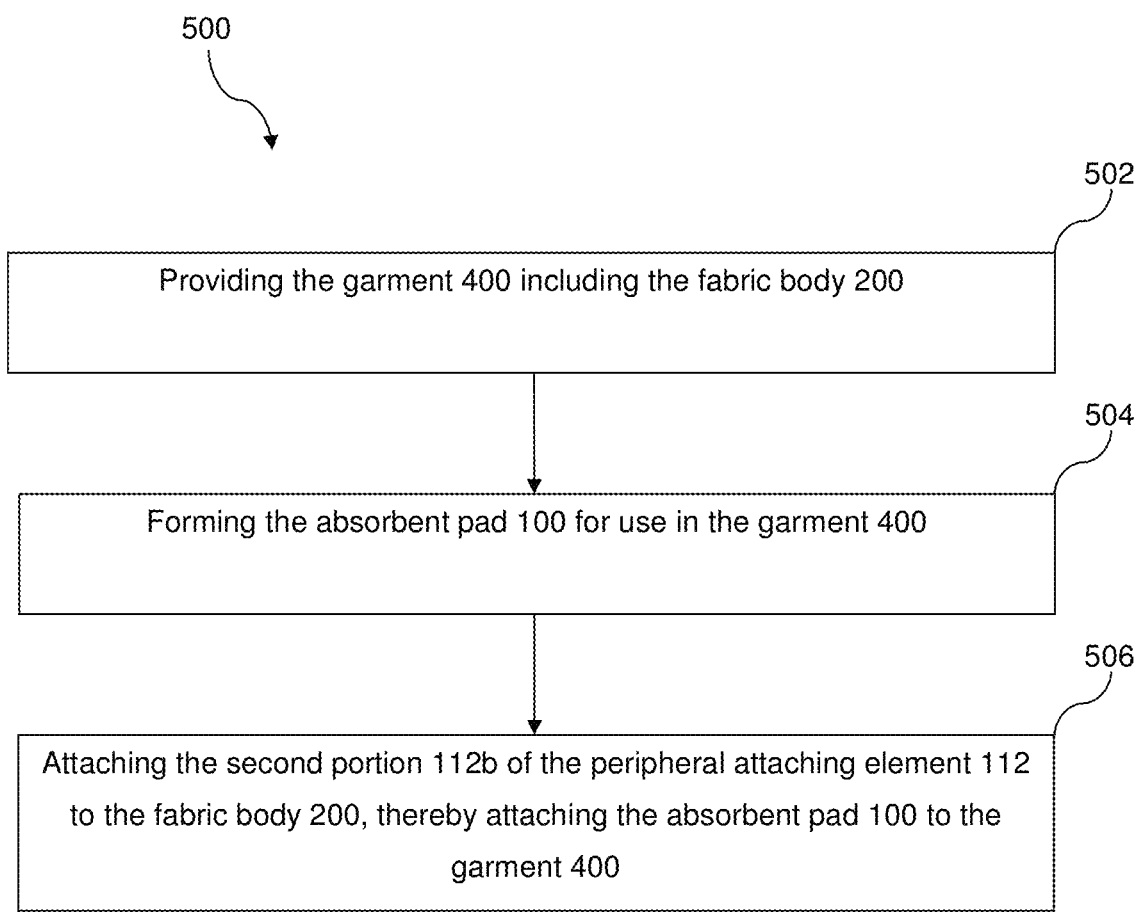
FIG. 5 is a flowchart illustration of a method for modifying a garment with the absorbent pad, in accordance with some embodiments of the present disclosure.

FIG. 5 shows the method 500 for modifying a garment 400 to include or be fitted with the absorbent pad 100. The method 500 includes a step 502 of providing the garment 400 including the fabric body 200. The method 500 further includes a step 504 of forming the absorbent pad 100 for use in the garment 400. The absorbent pad 100 is formed according to the method 300 described above and will not be further elaborated for purpose of brevity.

Figure 6A:
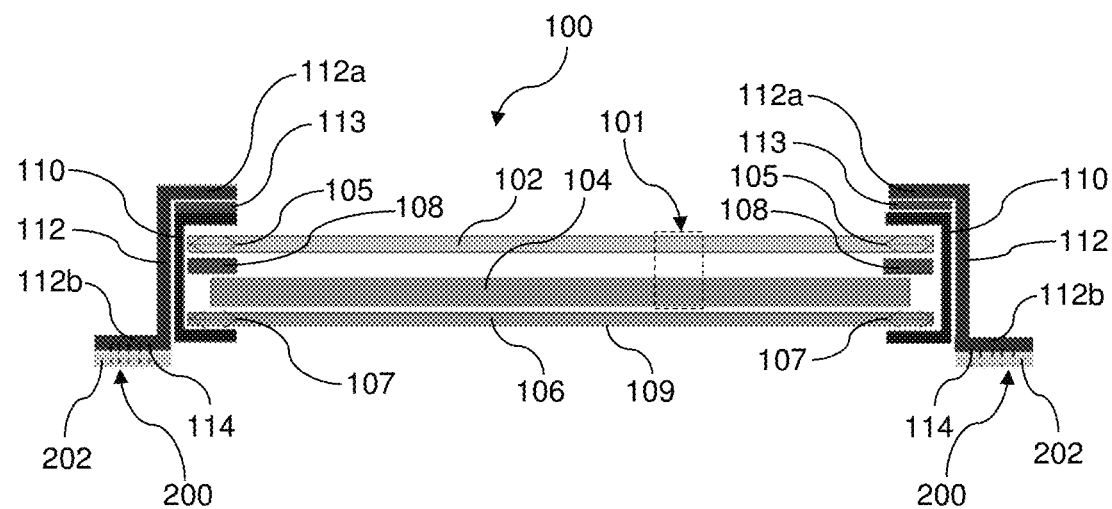
FIG. 6A to FIG. 6F are various cross-sectional and plan view illustrations of the garment being modified with the absorbent pad, in accordance with some embodiments of the present disclosure.
Figure 6B:
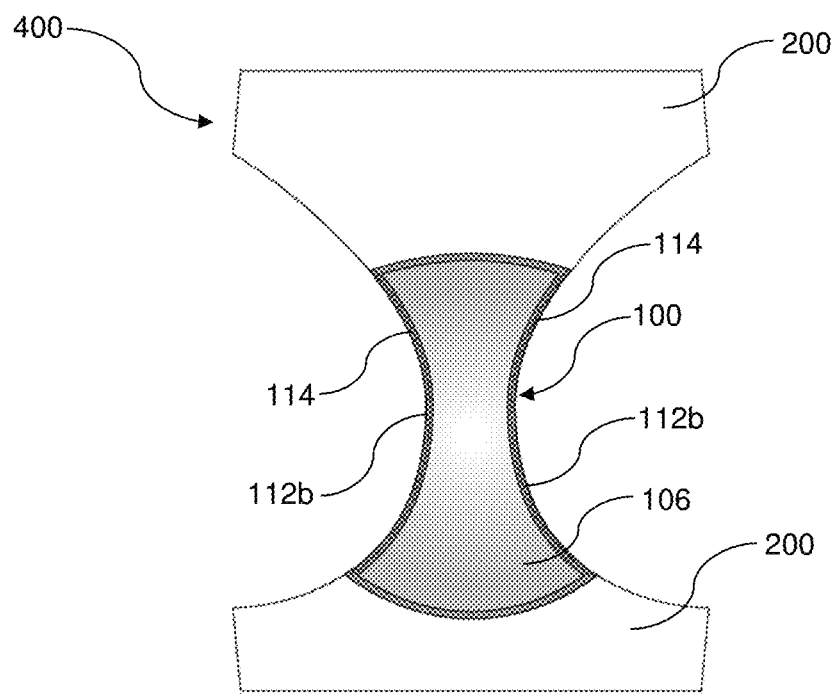

The method 500 further includes a step 506 of attaching the second portion 112b of the peripheral attaching element 112, which is detached from the peripheral sealing element 110, to the fabric body 200 of the garment 400, thereby attaching the absorbent pad 100 to the garment 400. In some embodiments as shown in FIG. 6A and FIG. 6B, the second portion 112b is attached to the fabric body 200 by stitching or sewing. Said stitching or sewing forms stiches 114 between the second portion 112b and the fabric body 200. Moreover, said stitching may be performed using the bag out method such as by single needle tacking. The bag out method can be defined, in a non-limiting manner, as sewing the fabric pieces inside out, and then turning everything right side out so all the seams, seam allowance and stitching is on the inside of the resultant fabric composite or garment 400.

In the bag out method for stitching, the absorbent pad 100 is placed on the fabric body 200 such that the barrier layer 106 is exposed, resulting in an inside out arrangement. The stitches 114 are then formed, such as by single needle tacking. As shown in FIG. 6A, the fabric body 200 has an edge 202 that is folded inwards for stitching with the second portion 112b along the side edges of the absorbent pad 100 using the bag out method. Stitching or sewing using the bag out method and along the edge 202 allows the resultant stitches 114 to be hidden from the user or other observer when the garment 400 is worn. By hiding the stiches 114 from view, the garment 400 is able to achieve an aesthetically pleasing appearance.

Figure 6C:
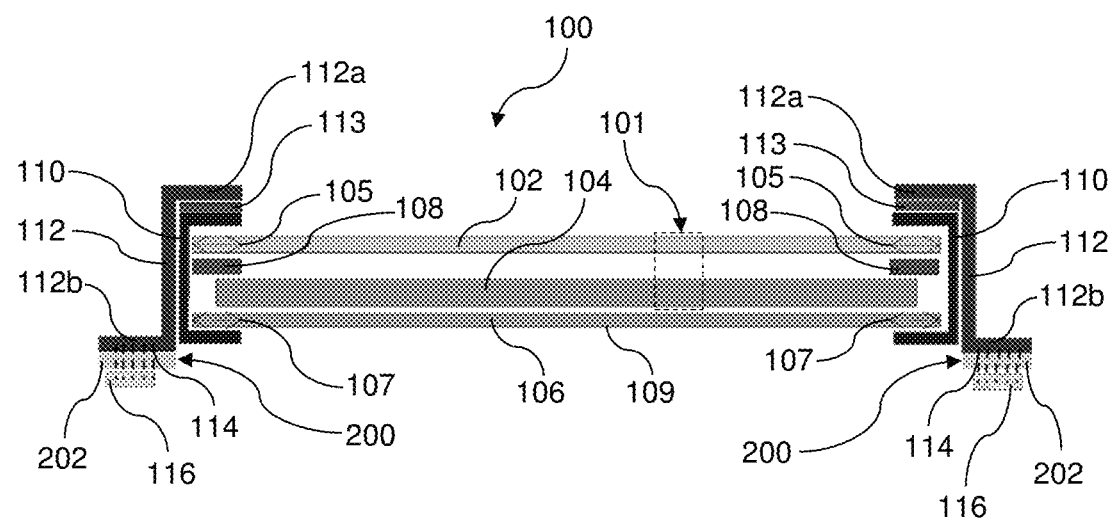
Figure 6D:
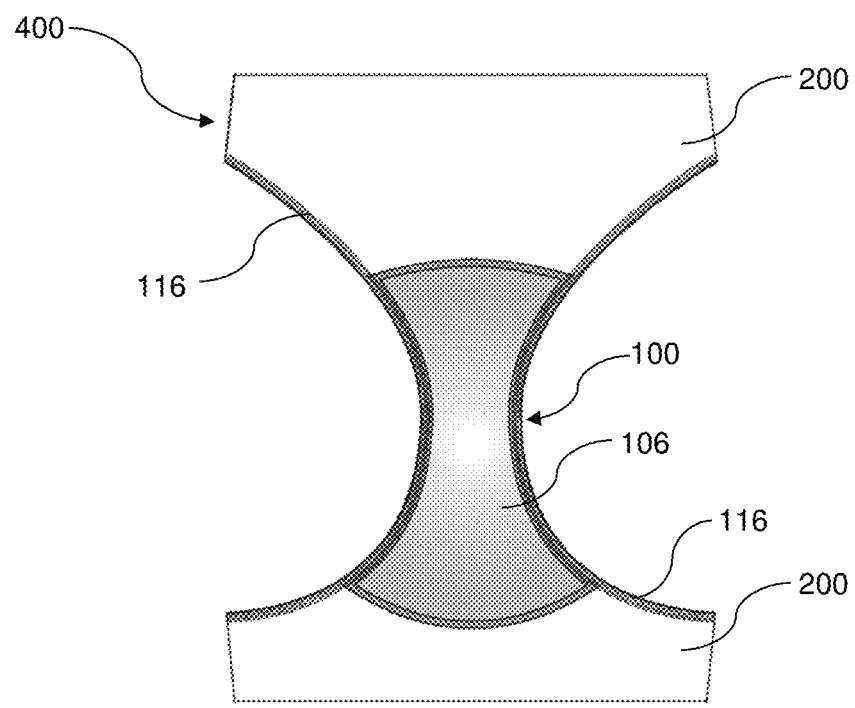

In some embodiments as shown in FIG. 6C and FIG. 6D, the fabric body 200 is attached with one or more elastic bands 116, such as by lining or inserting the elastic bands 116, to provide flexibility/elasticity to the user. This allows the garment 400 to come in a small number of discrete sizes that are able to cater to a wide variety of users of various sizes. For example, the garment 400 is a pair of underpants and the elastic bands 116 are arranged to surround the leg openings. In one embodiment, the elastic bands 116 are inserted before stitching or sewing the absorbent pad 100 to the fabric body 200, the absorbent pad 100 is stitched or sewed to the fabric body 200 together with the elastic bands 116. In another embodiment, the absorbent pad 100 is stitched to the fabric body 200 first, and the elastic bands 116 are attached to the fabric body 200 afterwards.

Figure 6E:
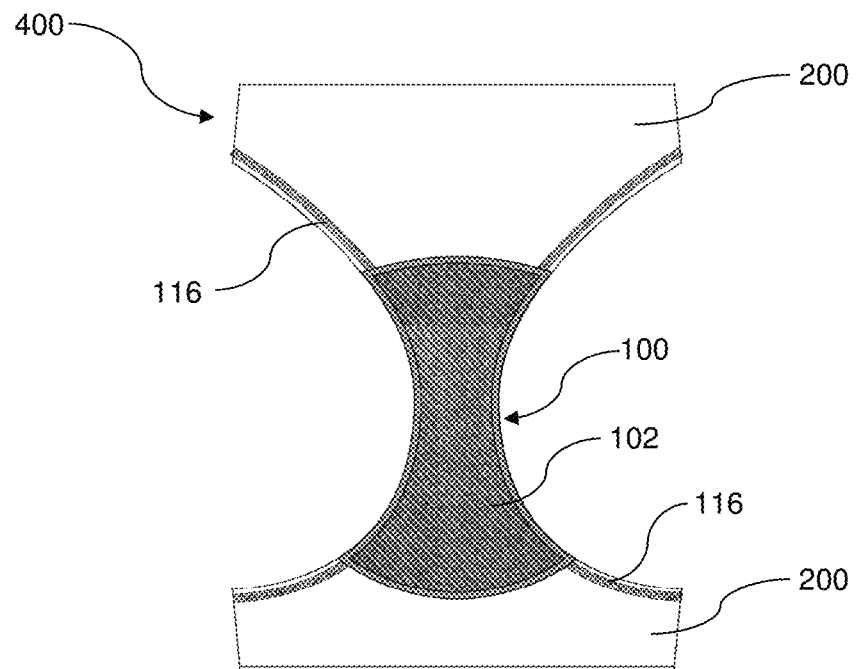
Figure 6F:
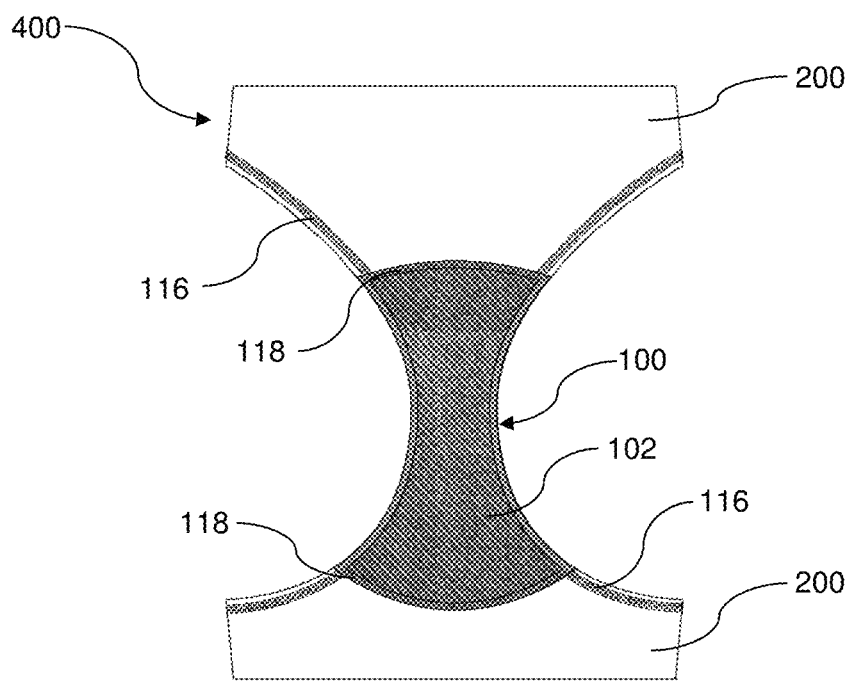
Figure 7A:
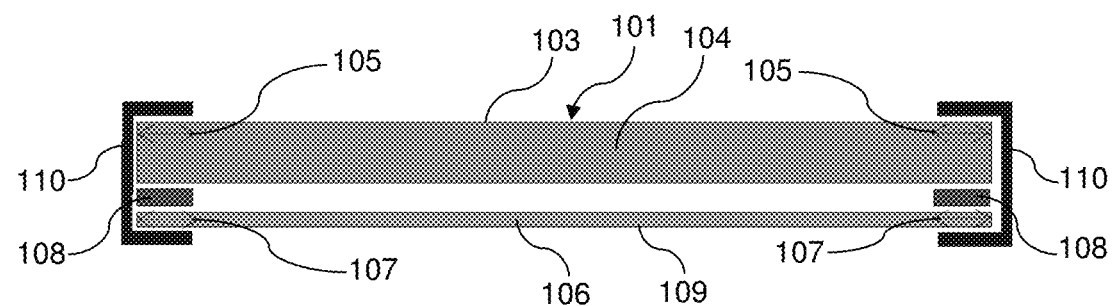
FIG. 7A to FIG. 7D are various other cross-sectional illustrations of the absorbent pad being formed and the garment being modified with the absorbent pad, in accordance with some embodiments of the present disclosure.
Figure 7B:
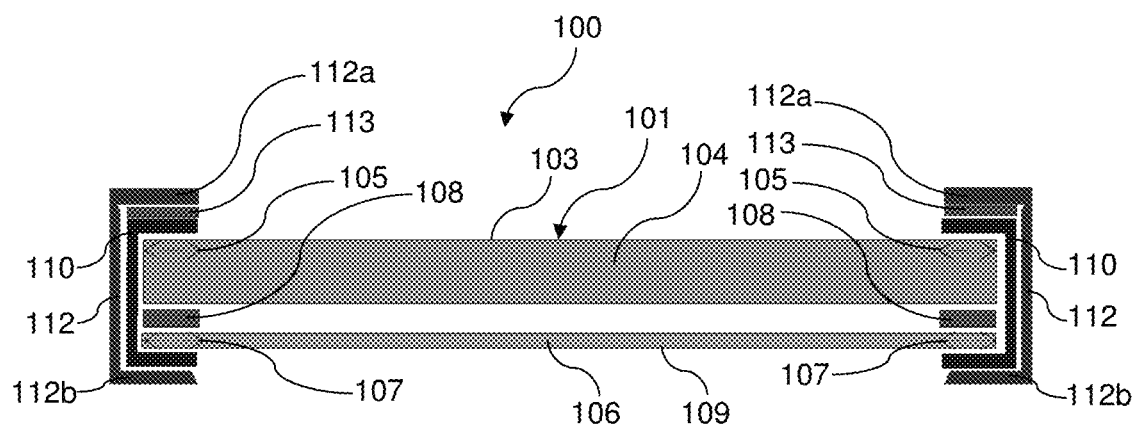
Figure 7C:
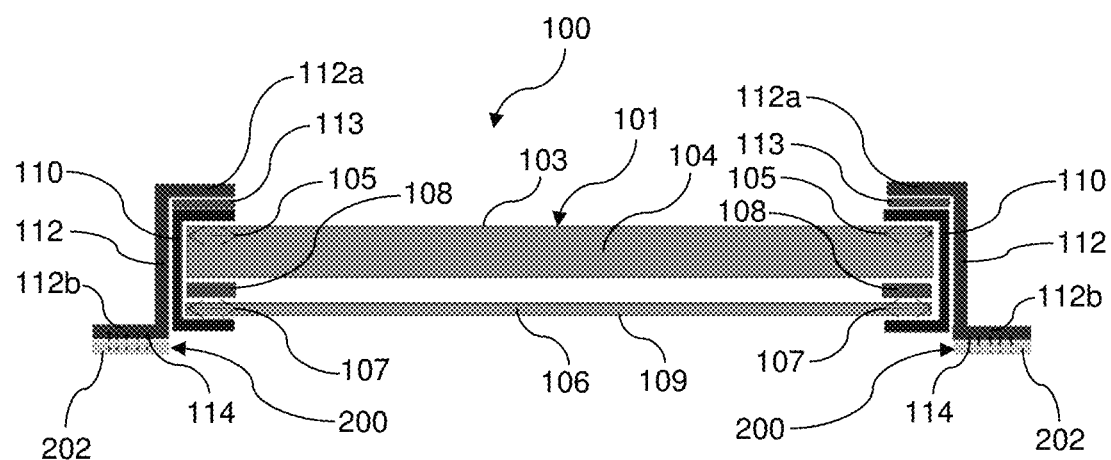
Figure 7D:
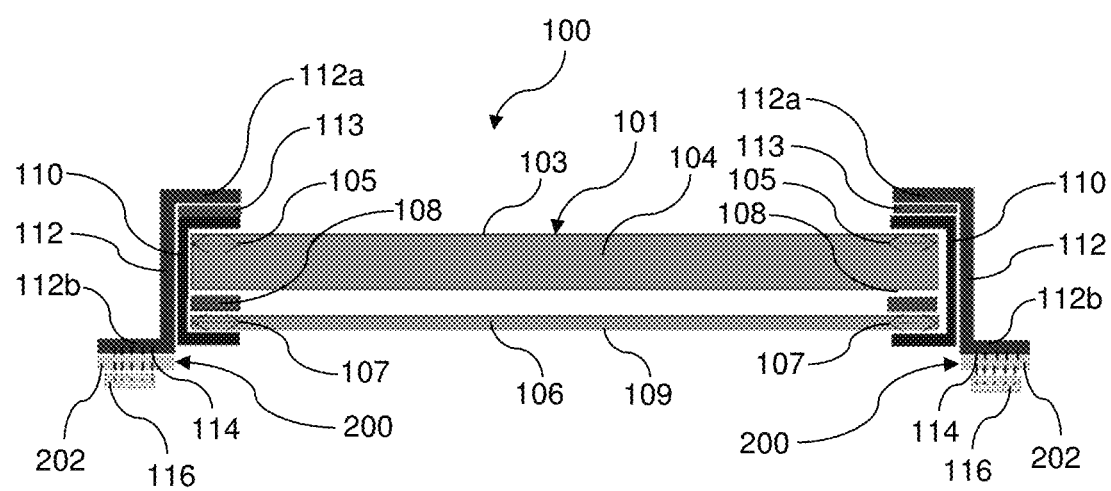

After stitching the absorbent pad 100 to the fabric body 200, the fabric body 200 is turned right side out as shown in FIG. 1 and FIG. 2. By turning the fabric body 200 right side out as shown in FIG. 6E, the barrier layer 106 is now in contact with the fabric body 200 and the functional layer 101/wicking component 102 is exposed. Notably, the functional layer 101/wicking component 102 should extend over an area of the user that is subject to bodily excretions. Additional stitches 118 may be formed to further secure the absorbent pad 100 to the fabric body 200, such as along the top and bottom edges of the absorbent pad 100 as shown in FIG. 6F.

In some embodiments, in the step 506, the second portion 112b is attached to the fabric body 200 by bonding them together and optionally without stitches. Said bonding may be by adhesive or ultrasonic bonding which are described above for the bonding means 108/113 and will not further elaborated or purpose of brevity. It will be appreciated that various aspects of the bag out method and the inclusion of the elastic bands 116 described above may apply similarly or analogously to these embodiments of bonding the second portion 112b to the fabric body 200. For example, the second portion 112b may be bonded to the fabric body 200 using a similar bag out method to achieve an aesthetically pleasing appearance, and the elastic bands 116 may be bonded to the fabric body 200, such as by adhesive or ultrasonic bonding and optionally without stitches.

In some embodiments, the absorbent pad 100 as shown in FIG. 2 has the functional layer 101 which includes the absorbent component 104 but excludes the wicking component 102. The method 300 for forming the absorbent pad 100 including said functional layer 101 as well as the method 500 for modifying the garment 400 to include said absorbent pad 100 are illustrated in FIG. 7A to FIG. 7D. It will be appreciated that various aspects of the methods 300 and 500 described above for the absorbent pad 100 will apply similarly or analogously for the embodiments as shown in FIG. 7A to FIG. 7D.

Figure 8A:
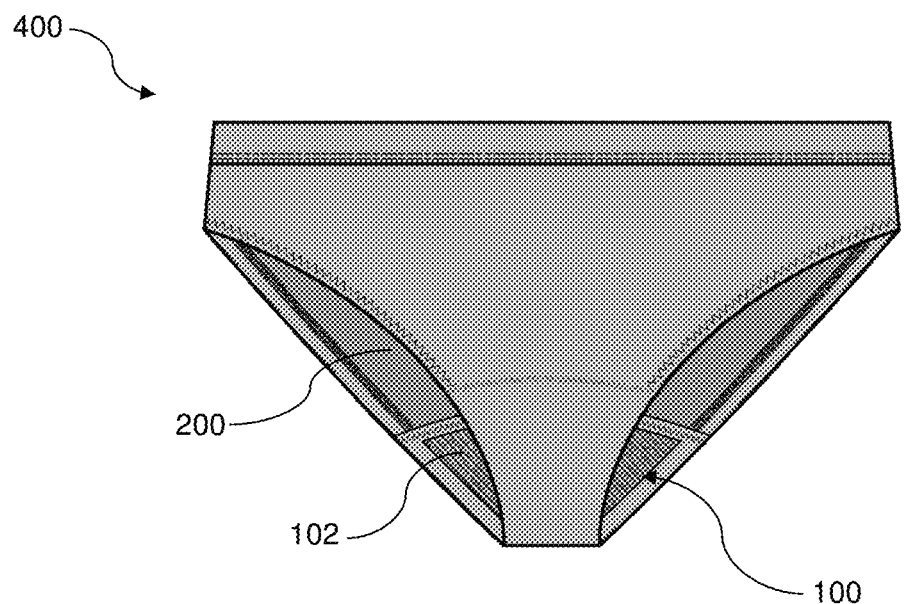
FIG. 8A and FIG. 8B are front view and rear view illustrations of the garment comprising the absorbent pad, in accordance with some embodiments of the present disclosure.
Figure 8B:
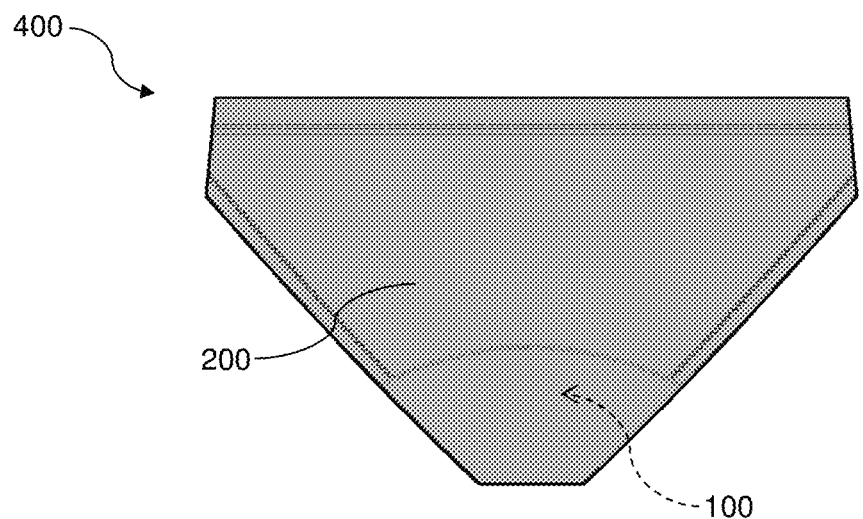

FIG. 8A and FIG. 8B show the final garment 400 modified by the method 500 to include or be fitted with the absorbent pad 100 that is attached to the fabric body 200. The absorbent pad 100 is leak-proof and enables the efficient transport of liquid from the surface of the absorbent pad 100, such as the wicking component 102 or outer surface 103 of the functional layer 101, to the underlying absorbent component 104. The garment 400 fitted with the absorbent pad 100 also exhibits the properties associated with the absorbent pad 100. For example, as the absorbent pad 100 provides sufficient and effective liquid absorption, when the garment 400 fitted with the absorbent pad 100 is in the form of an undergarment, there may be no need to use a disposable tampon/pad in conjunction with the undergarment. Further, the absorbent pad 100 is thinner than conventional products, enabling the garment 400 to be more attractive and more comfortable to wear than garments containing conventional pads, while providing enhanced protection from leakage. Although FIG. 8A and FIG. 8B show the garment 400 to be a pair of underpants, this should not be considered as limiting because similar arrangements may be used with respect to other types of garments 400.

Figure 9A:
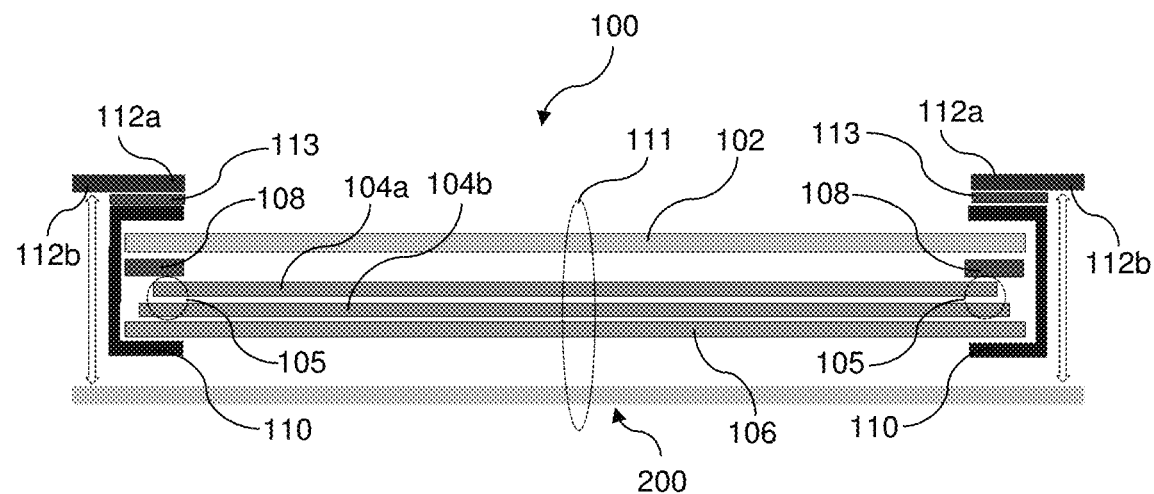
FIG. 9A and FIG. 9B are cross-sectional and plan view illustrations of another garment comprising the absorbent pad, in accordance with some embodiments of the present disclosure.

Depending on the configuration of the absorbent pad 100, one or more of the functional layer 101, wicking component 102, and absorbent component 104 may be stitched at their respective middle section 111 as shown in FIG. 9A. In some configurations, the functional layer 101, wicking component 102, and/or absorbent component 104 is itself formed from separate halves that are joined together at the middle section 111 by stitching. The stitch may be, but is not limited to, in the form of a single stitch, a double stitch, or a lock stitch. Having these stitches at the middle section 111 compresses the respective layers and components and creates a well-like or pocket-like profile at the middle section 111.

In some embodiments, the absorbent component 104 is formed from a composite of a plurality of absorbent layers. As shown in FIG. 9A, the absorbent component 104 has a first absorbent layer 104a and a second absorbent layer 104b. It will be appreciated that each of the absorbent layers 104ab is formed from an absorbent material described above for the absorbent component 104. The absorbent layers 104ab may be identically or non-identically sized. For example, FIG. 9A shows that the first absorbent layer 104a has a smaller footprint than the second absorbent layer 104b. Both absorbent layers 104ab may be joined together at their peripheries 105, such as by stitching and/or bonding.

As shown in FIG. 9A, the wicking component 102 and absorbent layers 104ab may be joined together at the middle section 111, such as by stitching and/or bonding. For example, the wicking component 102 and absorbent layers 104ab may be stitched together at the middle section 111, achieving a flat seam when viewed at the wicking component 102. Notably, the stitch does not penetrate the barrier layer 106 to keep it intact. The stitch may be, but is not limited to, in the form of a single stitch, a double stitch, or a lock stitch. The barrier layer 106 may join to the absorbent component 104, specifically the second absorbent layer 104b, at the middle section 111 using non-stitching means such as bonding to keep the barrier layer 106 intact. For example, ultrasonic bonding or an adhesive such as liquid glue or hotmelt powder glue may be used to bond or adhere the barrier layer 106 to the second absorbent layer 104b at the middle section 111. In some configurations, the barrier layer 106 is formed from separate halves that are joined together at the middle section 111 by ultrasonic bonding, and this bonding area at the middle section 111 is reinforced with reinforcement tape. It will be appreciated that this joining at the middle section 111 can apply similarly or analogously to other embodiments having various configurations of the functional layer 101, wicking component 102, and absorbent component 104 as described above.

Figure 9B:
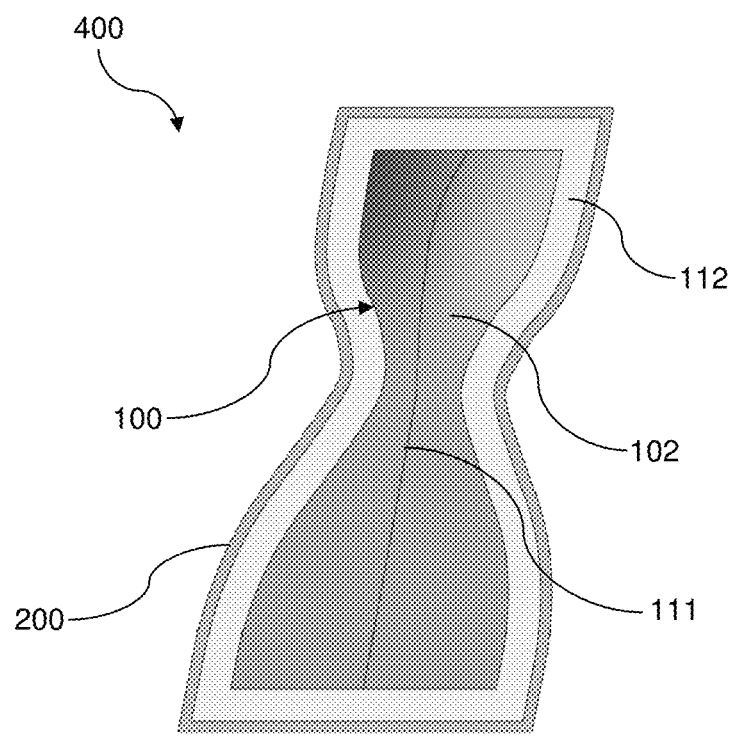

The absorbent pad 100 is attached to the garment 400 by stitching or bonding the second portion 112b of the peripheral attaching element 112 to the fabric body 200. FIG. 9B shows the final garment 400 fitted with the absorbent pad 100. The barrier layer 106 may join to the fabric body 200 at the middle section 111 using non-stitching means such as ultrasonic bonding and optionally reinforced with reinforcement tape. Like the absorbent pad 100, the fabric body 200 may include a stitch at the middle section 111 to compress the fabric body 200 and achieve the well-like or pocket-like profile at the middle section 111. Joining the various components and layers together at the middle section 111 allows the combination of the absorbent pad 100 and fabric body 200 to be more tightly compressed, thereby creating the well-like or pocket-like profile at the middle section 111. This well-like or pocket-like profile of the absorbent pad 100 and fabric body 200 makes the garment 400 suitable for use as men's undergarments or male urinary incontinence garments.

Figure 10A:
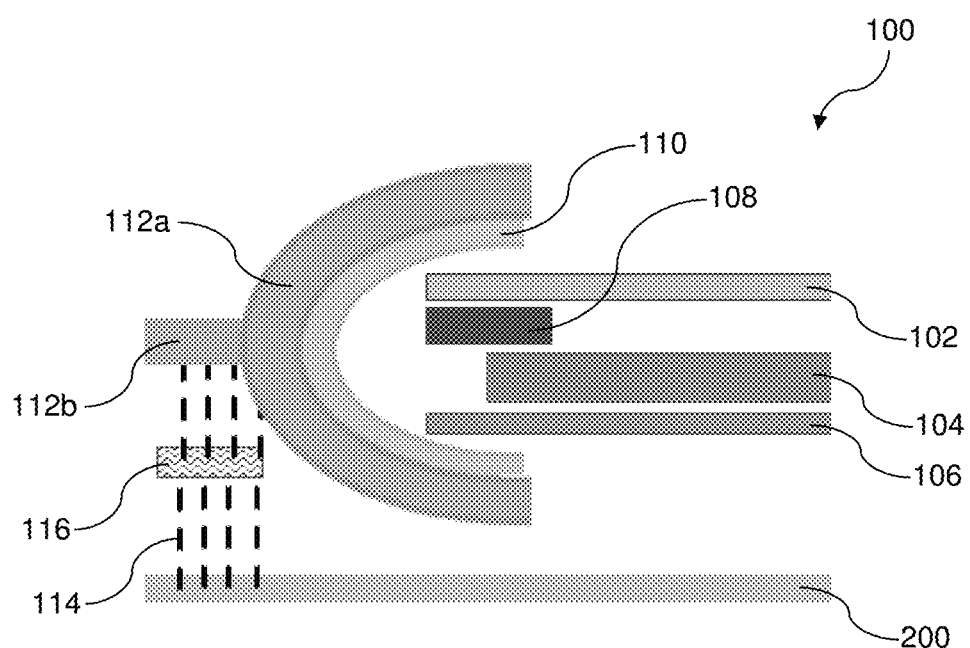
FIG. 10A and FIG. 10B are various other cross-sectional illustrations of an absorbent pad attached to a fabric body of a garment, in accordance with some embodiments of the present disclosure.
Figure 10B:
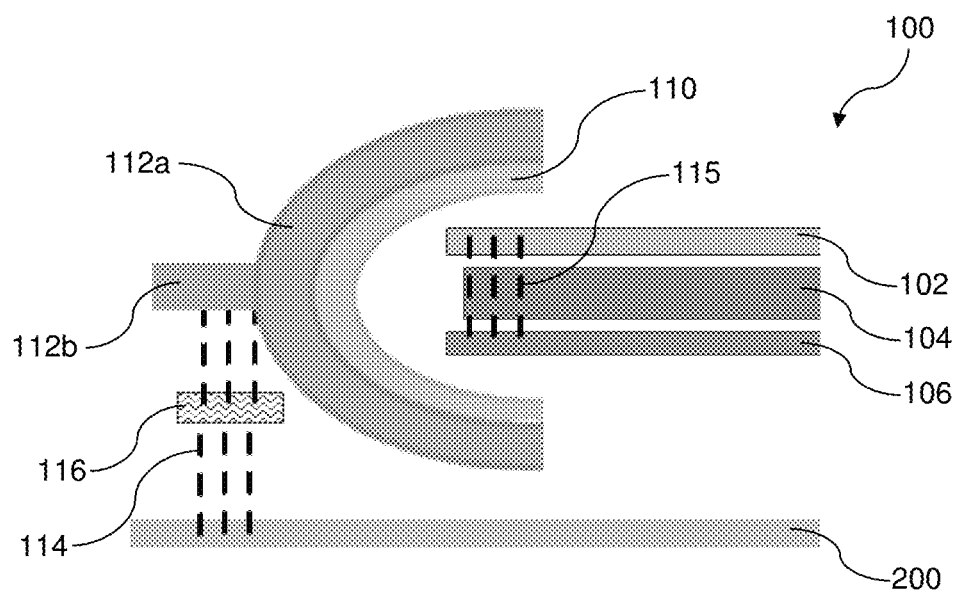

In some embodiments as shown in FIG. 10A and FIG. 10B, the peripheral attaching element 112 has a Y-shaped structure. The first portion 112a is bonded to the peripheral sealing element 110 and the second portion 112b is detached from the peripheral sealing element 110 for attaching to the fabric body 200. In one embodiment as shown FIG. 10A, the wicking component 102, absorbent component 104, and barrier layer 106 are bonded together using the bonding means 108. In another embodiment, the wicking component 102, absorbent component 104, and barrier layer 106 are stitched together at their peripheries and the Y-shaped peripheral sealing element 110 is arranged to overlap the stitches 115. For a male urinary incontinence garment, the barrier layer 106 is preferably bonded to the wicking component 102 and absorbent component 104 instead of stitching.

The peripheral sealing element 110 may be or include a double-sided adhesive tape. One adhesive side faces the wicking component 102, absorbent component 104, and barrier layer 106, while the other adhesive side faces the first portion 112a of the peripheral attaching element 112. Alternatively, the peripheral sealing element 110 may be or include a single-sided adhesive tape and the first portion 112a of the peripheral attaching element 112 is bonded to the non-adhesive side of the peripheral sealing element 110. The Y-shaped peripheral attaching element 112 may be integrally formed with the peripheral sealing element 110 and bonded to the wicking component 102 and barrier layer 106 as an integral element. This saves time in forming the absorbent pad 100.

The Y-shaped peripheral attaching element 112 may be formed of an elastic material, such as an elastic fabric or textile material, to facilitate attaching to the fabric body 200. However, it will be appreciated that the Y-shaped peripheral attaching element 112 can be formed of non-fabric/non-elastic materials as well. The absorbent pad 100 with the Y-shaped peripheral attaching element 112 is suitable for use in various urinary incontinence garments. It will be appreciated that the Y-shaped peripheral attaching element 112 can apply similarly or analogously to other embodiments having various configurations of the functional layer 101, wicking component 102, and absorbent component 104 as described above.

In some embodiments, the absorbent pad 100 and/or the garment 400 may be made to be washable and reusable, thereby helping to reduce environmental impact. For example, the absorbent pad 100 and/or the garment 400 is able to withstand at least 30 (e.g. a minimum of 50 or 100) machine wash and tumble dry cycles without change in overall appearance, integrity of the components (including the various layers, bonding, and adhesives) and liquid management parameters as discussed herein. The material selection and unique construction ensures that the absorbent pad 100 and/or the garment 400 are washable without compromising on one or more of moisture management, antimicrobial functionality, and anti-odour functionality.

Further, the integrity of the absorbent pad 100 may be maintained for a minimum of 30 (e.g. a minimum of 50 or 100) wash and dry cycles. This ensures that the absorbent pad 100 will not leak during the lifetime of the garment 400. For example, the various layers/components of the absorbent pad 100 described herein are chosen such that they remain chemically, thermally and mechanically stable throughout the intended lifetime of the absorbent pad 100/garment 400 while undergoing up to 30 (e.g. up to 50 or up to 100) wash and dry cycles.

Various components of the absorbent pad 100 may be made of a material that is heat stable up to 190° C., such as up to 95° C. The adhesive or ultrasonic bonding may be heat stable up to 190° C. or 95° C., which enables the absorbent pad 100 to be used in a garment 400 that can be washed and dried multiple times. Unless otherwise specified, used herein, the term "heat stable" is intended to stipulate that there is no change in the physical state of the component in question after being subjected to the stated temperature for a period of time consistent with a machine drying cycle.

In the foregoing detailed description, embodiments of the present disclosure in relation to an absorbent pad 100 for use in a garment 400 are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

What is claimed is:

1. A garment comprising:
   a fabric body; and
   an absorbent pad attached to the fabric body, the absorbent pad comprising:
      a liquid impermeable barrier layer;
      a liquid impermeable sealing element; and
      a functional layer attached to the barrier layer, the functional layer having a wicking component and a liquid absorbent component, the liquid absorbent component disposed between the wicking component and the barrier layer,
      wherein the functional layer includes stitching between the wicking component and the absorbent component, and
      wherein the liquid impermeable sealing element is coupled to a periphery of the functional layer and a periphery of the barrier layer, and
   wherein the absorbent pad is washable and reusable.

2. The garment of claim 1, wherein at least one of the wicking component and the absorbent component of the functional layer is stitched to the barrier layer.

3. The garment of claim 2, wherein the liquid impermeable sealing element overlaps the stitches through the functional layer and the barrier layer.

4. The garment of claim 1, wherein an outer side or layer of the wicking component facing away from the absorbent component comprises larger pores than an inner side or layer of the wicking component facing towards the absorbent component to facilitate communication of liquid to the absorbent component.

5. The garment of claim 4, wherein the outer side or layer of the wicking component has hydrophobic properties and the inner side or layer of the wicking component has hydrophilic properties.

6. The garment of claim 1, wherein the absorbent pad comprises a material for acquiring and distributing liquid from the wicking component to the absorbent component.

7. The garment of claim 1, wherein the absorbent pad includes an attaching element that is attached to the fabric body.

8. The garment of claim 7, wherein the attaching element comprises a first portion attached to the absorbent pad and a second portion stitched to the fabric body.

9. The garment of claim 7, wherein the attaching element is stretchable.

10. The garment of claim 7, wherein the attaching element and/or the fabric body comprises a material that prevents leakage of fluids.

11. The garment of claim 1, wherein the fabric body comprises an outer fabric layer and an inner fabric layer attached to the outer fabric layer, the inner fabric layer disposed on an inner surface of the outer fabric layer.

12. The garment of claim 11, wherein the absorbent pad is attached to the inner fabric layer.

13. The garment of claim 11, wherein the inner fabric layer is stretchable.

14. An absorbent pad for use with a fabric body, the absorbent pad comprising:
 a liquid impermeable barrier layer;
 a liquid impermeable sealing element; and
 a functional layer attached to the barrier layer, the functional layer having a wicking component and a liquid absorbent component, the liquid absorbent component disposed between the wicking component and the barrier layer,
 wherein the functional layer includes stitching between the wicking component and the absorbent component, and
 wherein the liquid impermeable sealing element is coupled to a periphery of the functional layer and a periphery of the barrier layer, and
 wherein the absorbent pad is washable and reusable.

15. The absorbent pad of claim 14, wherein at least one of the wicking component and the absorbent component of the functional layer is stitched to the barrier layer.

16. The absorbent pad of claim 15, wherein the liquid impermeable sealing element overlaps the stitches through the functional layer and the barrier layer.

17. The absorbent pad of claim 14, wherein an outer side or layer of the wicking component facing away from the absorbent component comprises larger pores than an inner side or layer of the wicking component facing towards the absorbent component to facilitate communication of liquid to the absorbent component.

18. The absorbent pad of claim 17, wherein the outer side or layer of the wicking component has hydrophobic properties and the inner side or layer of the wicking component has hydrophilic properties.

19. The absorbent pad of claim 14, further comprising a material for acquiring and distributing liquid from the wicking component to the absorbent component.

20. The absorbent pad of claim 14, further comprising an attaching element for attaching to the fabric body.

21. The absorbent pad of claim 20, wherein the attaching element comprises a first portion attached to the absorbent pad and a second portion for stitching to the fabric body.

22. The absorbent pad of claim 20, wherein the attaching element is stretchable.

23. The absorbent pad of claim 20, wherein the attaching element comprises a material that prevents leakage of fluids.

24. The garment of claim 1, wherein the liquid impermeable sealing element is bonded to a periphery of the functional layer and a periphery of the barrier layer.

25. The absorbent pad of claim 14, wherein the liquid impermeable sealing element is bonded to a periphery of the functional layer and a periphery of the barrier layer.

\* \* \* \* \*